US008398980B2

(12) United States Patent
Kano et al.

(10) Patent No.: US 8,398,980 B2
(45) Date of Patent: Mar. 19, 2013

(54) SUBTYPES OF HUMANIZED ANTIBODY AGAINST INTERLEUKEN-6 RECEPTOR

(75) Inventors: Katsuhiro Kano, Tokyo (JP); Isamu Terashima, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 552 days.

(21) Appl. No.: 10/593,786

(22) PCT Filed: Mar. 24, 2005

(86) PCT No.: PCT/JP2005/006229
§ 371 (c)(1),
(2), (4) Date: Aug. 26, 2008

(87) PCT Pub. No.: WO2005/090405
PCT Pub. Date: Sep. 29, 2005

(65) Prior Publication Data
US 2010/0247523 A1    Sep. 30, 2010

(30) Foreign Application Priority Data

Mar. 24, 2004  (JP) ................................. 2004-087578

(51) Int. Cl.
*A61K 39/395* (2006.01)
*C12P 21/08* (2006.01)
*C07K 16/00* (2006.01)
*C07K 16/24* (2006.01)

(52) U.S. Cl. ............... 424/145.1; 424/130.1; 424/133.1; 424/141.1; 530/387.1; 530/387.3; 530/388.1; 530/388.23

(58) Field of Classification Search .................. None
See application file for complete search history.

(56) References Cited

U.S. PATENT DOCUMENTS

| | | | |
|---|---|---|---|
| 5,126,250 A | 6/1992 | McDonough et al. | |
| 5,171,840 A | 12/1992 | Kishimoto | |
| 5,216,128 A | 6/1993 | Novick et al. | |
| 5,480,796 A | 1/1996 | Kishimoto | |
| 5,670,373 A | 9/1997 | Kishimoto | |
| 5,795,965 A | 8/1998 | Tsuchiya et al. | |
| 5,817,790 A | 10/1998 | Tsuchiya et al. | |
| 5,851,793 A | 12/1998 | Kishimoto | |
| 5,888,510 A | 3/1999 | Kishimoto et al. | |
| 5,990,282 A | 11/1999 | Kishimoto | |
| 5,994,511 A | 11/1999 | Lowman et al. | |
| 6,086,874 A | 7/2000 | Yoshida et al. | |
| 6,261,560 B1 | 7/2001 | Tsujinaka et al. | |
| 6,401,691 B1 | 6/2002 | Kawano et al. | |
| 6,406,909 B1 | 6/2002 | Shibuya et al. | |
| 6,428,979 B1 | 8/2002 | Kishimoto | |
| 6,537,782 B1 | 3/2003 | Shibuya et al. | |
| 6,692,742 B1 | 2/2004 | Nakamura et al. | |
| 6,723,319 B1 | 4/2004 | Ito et al. | |
| 6,962,812 B2 | 11/2005 | Shibuya et al. | |
| 7,320,792 B2 | 1/2008 | Ito et al. | |
| 7,332,289 B2 | 2/2008 | Takeda et al. | |
| 7,479,543 B2 | 1/2009 | Tsuchiya et al. | |
| 7,498,031 B2 | 3/2009 | Fujioka et al. | |
| 7,521,052 B2 | 4/2009 | Okuda et al. | |
| 7,566,453 B2 | 7/2009 | Nakamura et al. | |
| 7,771,723 B2 | 8/2010 | Nakamura et al. | |
| 7,824,674 B2 | 11/2010 | Ito et al. | |
| 7,927,815 B2 | 4/2011 | Takeda et al. | |
| 7,955,598 B2 | 6/2011 | Yoshizaki et al. | |
| 8,017,121 B2 | 9/2011 | Kishimoto et al. | |
| 8,173,126 B2 | 5/2012 | Yoshizaki et al. | |
| 2003/0190316 A1 | 10/2003 | Kakuta et al. | |
| 2005/0118163 A1 | 6/2005 | Mizushima et al. | |
| 2005/0214278 A1 | 9/2005 | Kakuta et al. | |
| 2006/0134113 A1 | 6/2006 | Mihara | |
| 2006/0142549 A1 | 6/2006 | Takeda et al. | |
| 2006/0165696 A1 | 7/2006 | Okano et al. | |
| 2006/0292147 A1 | 12/2006 | Yoshizaki et al. | |
| 2007/0036785 A1 | 2/2007 | Kishimoto et al. | |
| 2007/0098714 A1 | 5/2007 | Nishimoto et al. | |
| 2008/0124325 A1 | 5/2008 | Ito et al. | |
| 2008/0124761 A1 | 5/2008 | Goto et al. | |
| 2008/0274106 A1 | 11/2008 | Nishimoto et al. | |
| 2008/0306247 A1 | 12/2008 | Mizushima et al. | |
| 2009/0022719 A1 | 1/2009 | Mihara et al. | |
| 2009/0131639 A1 | 5/2009 | Kakuta et al. | |
| 2009/0181029 A1 | 7/2009 | Okuda et al. | |
| 2009/0220499 A1 | 9/2009 | Yasunami | |

(Continued)

FOREIGN PATENT DOCUMENTS

| | | |
|---|---|---|
| EP | 0 628 639 | 12/1994 |
| FR | 2 694 767 | 2/1994 |

(Continued)

OTHER PUBLICATIONS

Harris, R.(1995). "Processing of C-terminal lysine and arginine residues of proteins isolated from mammalian cell culture." *Journal of Chromatography A*.705:129-134.
Hirano, T. et al. (Nov. 6, 1986)."Complementary DNA for a novel human interleukin (BSF-2) that induces B lymphocytes to produce immunoglobulin." *Nature*. 324:73-76.
Akira, S., et al., (1993). "Interleukin-6 in Biology and Medicine." *Advances in Immunology*. 54:1-78.
Lotz, M. et al. (Mar. 1, 1988) "B Cell Stimulating Factor 2/Interleukin 6 is a Costimulant for Human Thymocytes and T Lymphocytes." *J. Exp. Med*.:167:1253-1258.
Taga, T. et al. (Oct. 1, 1987)."Receptors for B Cell Stimulatory Factor 2: Quantitation, Specificity, Distribution, and Regulation of Their Expression." *J. Exp. Med*.:166:967-981.
Yamasaki, K. et al. (Aug. 12, 1988)."Cloning and Expression of the Human Interleukin-6 (BSF-2/IFNβ 2) Receptor." *Science*.241:825-828.

(Continued)

*Primary Examiner* — Christine J Saoud
*Assistant Examiner* — Jon M Lockard
(74) *Attorney, Agent, or Firm* — Morrison & Foerster LLP

(57) ABSTRACT

As a subtype of humanized PM-1 antibody against interleukin-6 receptor (IL-6R), there is provided antibody sub-type (1) whose one heavy chain C terminus consists of Pro-NH$_2$ (447). As another subtype of humanized PM-1 antibody against interleukin-6 receptor (IL-6R), there is provided antibody subtype (2) whose both heavy chain C termini consist of Pro-NH$_2$ (447). Furthermore, there are provided pharmaceutical compositions comprising these.

10 Claims, 24 Drawing Sheets

U.S. PATENT DOCUMENTS

| | | |
|---|---|---|
| 2009/0220500 A1 | 9/2009 | Kobara |
| 2009/0263384 A1 | 10/2009 | Okada et al. |
| 2009/0269335 A1 | 10/2009 | Nakashima et al. |
| 2009/0291076 A1 | 11/2009 | Morichika et al. |
| 2010/0008907 A1 | 1/2010 | Nishimoto et al. |
| 2010/0034811 A1 | 2/2010 | Ishida |
| 2010/0061986 A1 | 3/2010 | Takahashi et al. |
| 2010/0129355 A1 | 5/2010 | Ohguro et al. |
| 2010/0247523 A1 | 9/2010 | Kano et al. |
| 2010/0255007 A1 | 10/2010 | Mihara et al. |
| 2010/0285011 A1 | 11/2010 | Morichika et al. |
| 2010/0304400 A1 | 12/2010 | Stubenrauch et al. |
| 2011/0117087 A1 | 5/2011 | Franze et al. |
| 2011/0150869 A1 | 6/2011 | Mitsunaga et al. |
| 2011/0206664 A1 | 8/2011 | Yoshizaki et al. |
| 2011/0245473 A1 | 10/2011 | Igawa et al. |
| 2011/0262462 A1 | 10/2011 | Platt et al. |
| 2011/0268734 A1 | 11/2011 | Ito et al. |
| 2012/0009177 A1 | 1/2012 | Platt et al. |
| 2012/0183539 A1 | 7/2012 | Maeda |

FOREIGN PATENT DOCUMENTS

| | | |
|---|---|---|
| JP | 05-227970 A | 9/1993 |
| JP | 06-319396 A | 11/1994 |
| JP | 3630453 B | 3/1995 |
| JP | 7-188056 A | 7/1995 |
| JP | 08-099902 | 4/1996 |
| JP | 2002-510211 A | 4/2002 |
| JP | 2002-525104 A | 8/2002 |
| JP | 3-822137 A | 11/2003 |
| JP | 2009-092508 A | 4/2009 |
| WO | WO-00/03000 A2 | 1/2000 |
| WO | WO-00/03000 A3 | 1/2000 |
| WO | WO-00/10607 A1 | 3/2000 |
| WO | WO-00/18804 A1 | 4/2000 |
| WO | WO-02/13859 A1 | 2/2002 |
| WO | WO-2005/089802 A1 | 9/2005 |
| WO | WO-2005/090405 A1 | 9/2005 |
| WO | WO-2008/016134 A1 | 2/2008 |
| WO | WO-2008/078715 A1 | 7/2008 |
| WO | WO-2011/013786 A1 | 2/2011 |
| WO | WO-2011/149046 A1 | 12/2011 |
| WO | WO-2011/149051 A1 | 12/2011 |
| WO | WO-2012/064627 A2 | 5/2012 |
| WO | WO-2012/064627 A3 | 5/2012 |

OTHER PUBLICATIONS

Novick, D. et al. (Nov. 1, 1991). "Monoclonal Antibodies to the Soluble Human IL-6 Receptor: Affinity Purification, ELISA, and Inhibition of Ligand Binding." *Hybridoma.* 10:137-146.

Huang, Y, et al. (Nov. 5, 1993)."A Monoclonal Anti-Human IL-6 Receptor Antibody Inhibits the Proliferation of Human Myeloma Cells." *Hybridoma.* 12:621-630.

Sato, K. et al. (Feb. 15, 1993). "Reshaping a Human Antibody to Inhibit the Interleukin 6-dependent Tumor Cell Growth." *Cancer Research.*53:851-856.

Johnson, K. A. et al. (2007)."Cation exchange-HPLC and mass spectrometry reveal C-terminal amidation of an IgG1 heavy chain." *Analytical Biochemistry.*360:75-83.

International Search Report, mailed Jun. 7, 2005, directed to counterpart International Patent Application No. PCT/JP2005/006229; 2 pages.

(Aug. 1999). "Guidance for Industry:Q6B Specifications: Test Procedures and Acceptance Criteria for Biotechnological/Biological Products," U.S. Department of Health and Human Services; Food and Drug Administration; retrieved on Sep. 3, 2009 from the internet: http://www.fda.gov/downloads/Drugs/GuidanceComplianceRegulatoryInformation/Guidances/ucm073488.pdf; Table of Contents, 24 pages.

Supplementary European Search Report mailed on Sep. 23, 2009; directed to European Patent Application No. 05 72 7379; 4 pages.

Santora, L. C. (1999). "Characterization of Recombinant Human Monoclonal Tissue Necrosis Factor-α Antibody Using Cation-Exchange HPLC and Capillary Isoelectric Focusing," *Analytical Biochemistry* 275:98-108.

Lazar, A. C. (2004). "Matrix-assisted laser desorption/ionization mass spectrometry for the evaluation of the C-terminal lysine distribution of a recombinant monoclonal antibody," *Rapid Communications in Mass Spectrometry* 18:239-244.

Japanese Office Action mailed Jan. 25, 2011, directed to counterpart Japanese Application No. 2006-511350; 6 pages.

Adamczyk, M. et al. (2002). "Complete Sequencing of Antivancomycin Fab Fragment by Liquid Chromatography-electrospray Ion Trap Mass Spectrometry with a Combination of Database Searching and Manual Interpretation of the MS/MS Spectra," *Journal of Immunological Methods* 260:235-249.

Hirata, Y. et al. (1989). "Characterization of IL-6 Receptor Expression by Monoclonal and Polyclonal Antibodies," *The Journal of Immunology* 143(9):2900-2906.

Merkler, D. J. et al. (1991). "Recombinant Type A Rat 75-kDa α-Amidating Enzyme Catalyzes the Conversion of Glycine-Extended Peptides to Peptide Amides via an α-Hydroxyglycine Intermediate," *Archives of Biochemistry and Biophysics* 289(1):192-196.

Miller, D. A. et al. (1992). "Characterization of a Bifunctional Peptidylglycine α-Amidating Enzyme Expressed in Chinese Hamster Ovary Cells," *Archives of Biochemistry and Biophysics* 298(2):380-388.

Ray, M. V. L. et al. (2002). "Production of Salmon Calcitonin by Direct Expression of a Glycine-extended Precursor in *Escherichia coli,*" *Protein Expression and Purification* 26:249-259.

Antes, B. et al. (2007). "Analysis of Lysine Clipping of a Humanized Lewis-Y Specific IgG Antibody and Its Relation to Fc-Mediated Effector Function," *Journal of Chromatography B*, 852:250-256.

Clinicaltrials.Gov, (2005). "Phase III Comparative Study (Open-Label) of MRA for Rheumatoid Arthritis (RA)," Study Start Date Mar. 2003, Study first received on Sep. 2, 2005, Study Completion Date Feb. 2006, last updated Jan. 30, 2009, ClinicalTrials.gov Identifier: NCT00144508, Drug: MRA (Tocilizumab), with all results, last visited Sep. 19, 2012, 6 pages.

Clinicaltrials.Gov, (2005). "Comparative Study (Double-Blind) of MRA for Rheumatoid Arthritis (RA)," Study Start Date Feb. 2004, Study first received on Sep. 2, 2005, Study Completion Date, Apr. 2006, last updated Jan. 30, 2009, ClinicalTrials.gov Identifier: NCT00144521, Drug: MRA (Tocilizumab), with all results, last visited Sep. 19, 2012, 10 pages.

Clinicaltrials.Gov, (2005). "Study of MRA in Patients With Rheumatoid Arthritis (RA)," Study Start Date, Aug. 2001, Study first received on Sep. 2, 2005, Study Completion Date Jun. 2009, last updated Dec. 21, 2009, ClinicalTrials.gov Identifier: NCT00144651, Drug: MRA (Tocilizumab), with all results, last visited Sep. 19, 2012, 6 pages.

Johnson, K.A. et al. (2007, e-pub. Oct. 30, 2006). "Cation Exchange-HPLC and Mass-Spectrometry Reveal C-Terminal Amidation of an IgG1 Heavy Chain," *Analytical Biochemistry* 360:75-83.

U.S. Appl. No. 08/414,425, filed on Mar. 31, 1995, by Kawano.

U.S. Appl. No. 09/762,550, filed on Feb. 9, 2001, by Funakoshi.

U.S. Appl. No. 13/290,366, filed on Nov. 7, 2011, by Bao.

SUBTYPES OF HUMANIZED ANTIBODY AGAINST INTERLEUKEN-6 RECEPTOR

TECHNICAL FIELD

The present invention relates to novel subtypes of the humanized PM-1 antibody which is an antibody against interleukin-6 receptor (IL-6R).

BACKGROUND ART

Though proteins produced by gene recombinant technology should have an amino acid sequence predicted from the gene sequence, a number of variants may actually be produced. This is due to known or novel in vivo (post-transcription) modification or naturally occurring (non-enzymatic) proteolysis (R. J. Harris, J. Chromatogr. A 705 (1995) 129-134). Since proteins for use as ingredients of pharmaceutical drugs are produced by gene recombinant technology utilizing in vivo biosynthetic processes, there is a possibility that subtypes having different molecular structures may be produced. The kinds and contents of subtypes define the quality of pharmaceutical drugs, and therefore it is important to characterize the subtype profiles and assure their usefulness as pharmaceutical compositions.

IL-6 is a cytokine which is also called B cell stimulating factor 2 (BSF2) or interferon β2. IL-6 was discovered as a differentiation factor involved in the activation of B-lymphatic cells (Hirano, T. et al., Nature (1986) 324, 73-76). Thereafter, it was found to be a multifunctional cytokine that influences various functions of the cell (Akira, S. et al., Adv. in Immunology (1993) 54, 1-78). IL-6 has been reported to induce the maturation of T-lymphatic cells (Lotz, M. et al., J. Exp. Med. (1988) 167, 1253-1258).

IL-6 transmits its biological activity through two types of proteins on the cell. One type is interleukin-6 receptor (IL-6R), a ligand-biding protein with a molecular weight of about 80 kD, to which IL-6 binds (Taga, T. et al., J. Exp. Med. (1987) 166, 967-981; Yamasaki, K. et al., Science (1987) 241, 825-828). IL-6R occurs not only in the membrane-bound form that penetrates through and is expressed on the cell membrane but also as a soluble IL-6R consisting mainly of the extracellular region.

Anti-IL-6R antibody has been described in several reports (Novick D. et al., Hybridoma (1991) 10, 137-146, Huang; Y. W. et al., Hybridoma (1993) 12, 621-630; International Patent Publication WO 95-09873; French Patent Application FR 2694767; U.S. Pat. No. 521,628). A known Humanized PM-1 antibody was obtained by transplanting the complementarity determining region (CDR) of a mouse antibody PM-1 (Hirata, Y. et al., J. Immunol. (1989) 143, 2900-2906), to a human antibody (International Patent Publication WO 92-19759).

However, subtypes of the humanized PM-1 antibody are not known.
Patent document 1: WO 92/19759
Patent document 2: Japanese Unexamined Patent Publication (Kokai) No. 8-99902
Patent document 3: French Patent Publication FR 2694767
Patent document 4: U.S. Pat. No. 521,628
Non-patent document 1: R. J. Harris, J. Chromatogr. A 705 (1995) 129-134
Non-patent document 2: Hirano, T. et al., Nature (1986) 324, 73-76
Non-patent document 3: Akira, S. et al., Adv. in Immunology (1993) 54, 1-78
Non-patent document 4: Lotz, M. et al., J. Exp. Med. (1988) 167, 1253-1258
Non-patent document 5: Taga, J. Exp. Med. (1987) 166, 967-981
Non-patent document 6: Yamasaki, K. et al., Science (1987) 241, 825-828
Non-patent document 7: Novick, D. et al., Hybridoma (1991) 10, 137-146
Non-patent document 8: Huang, Y. W. et al., Hybridoma (1993) 12, 621-630
Non-patent document 9: Hirata, Y. et al., J. Immunol. (1989) 143, 2900-2906

DISCLOSURE OF THE INVENTION

Thus, the present invention relates to novel subtypes of the humanized PM-1 antibody and a pharmaceutical composition comprising said subtypes.

After careful separation of the recombinantly produced humanized PM-1 antibody, the present inventors have found that there is a molecular species in which Gly at the C-terminal (position 448) of the constant region constituting the heavy chain of the humanized PM-1 antibody is lost and Pro at position 447 has been amidated, as well as an antibody subtype (referred to as subtype 1) in which only one of the two heavy chains constituting the antibody has been amidated and an antibody subtype (referred to as subtype 2) in which both have been amidated. Furthermore, the present inventors have found that both of the above subtypes retain the same antigen-binding activity and cell growth-inhibiting activity as the native antibody in which the C-terminal is Gly (448), and have thus completed the present invention.

Thus, the present invention provides an antibody subtype (1) which is a subtype of the humanized PM-1 antibody against interleukin-6 receptor (IL-6R) and in which one C-terminal of the heavy chain is Pro-$NH_2$ (447), and an antibody subtype (2) which is a subtype of the humanized PM-1 antibody against interleukin-6 receptor (IL-6R) and in which both C-terminals of the heavy chain are Pro-$NH_2$ (447). The native heavy chain C-terminal of the humanized PM-1 antibody corresponding to both of the above subtypes is Gly (448). In a preferred embodiment, the native heavy chain corresponding to the amidated heavy chain subtype has the amino acid sequence set forth in SEQ ID NO: 1. In a preferred embodiment, glutamine (Gln) at the heavy chain N-terminal has been replaced with pyroglutamic acid (pGlu). Also, in a preferred embodiment, the light chain constituting the antibody subtype of the present invention has the amino acid sequence set forth in SEQ ID NO: 2.

The present invention also provides a pharmaceutical composition comprising either subtype (1) or subtype (2) described above, or both subtypes (1) and (2).

BEST MODE FOR CARRYING OUT THE INVENTION

Figure 1:
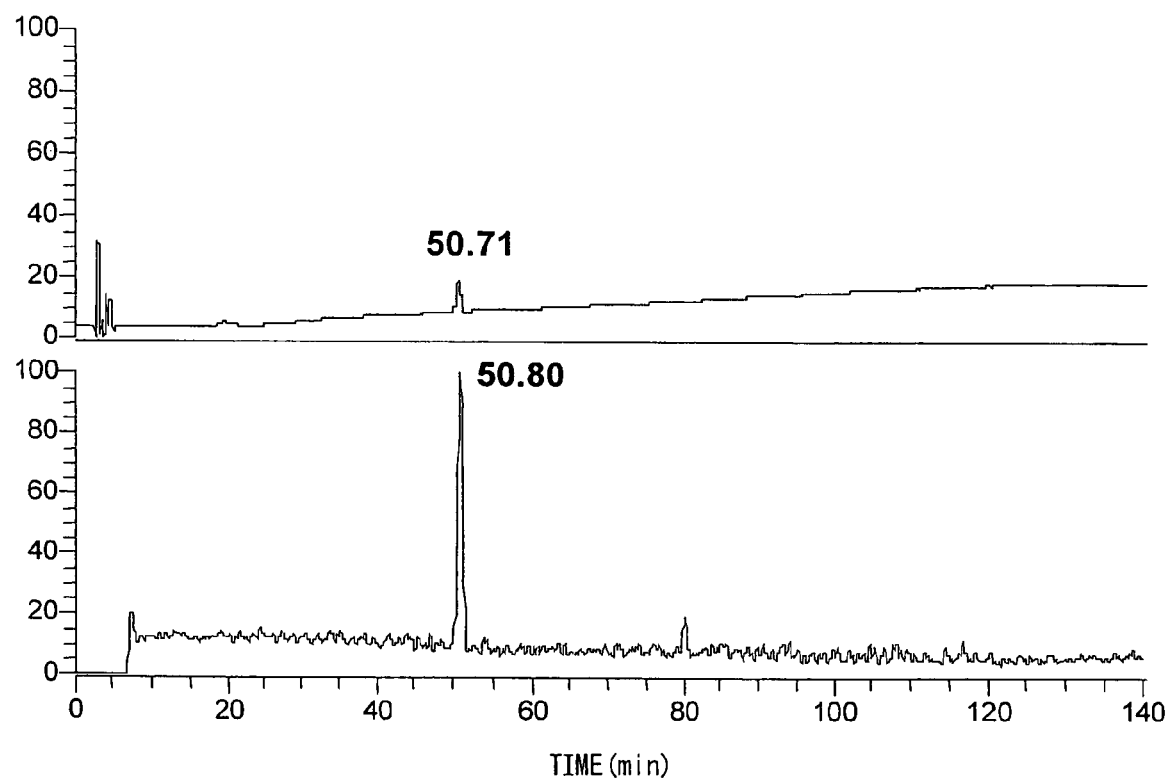
FIG. 1 shows the result of liquid chromatography in the liquid chromatography (LC)-mass spectrometry (MS) of the peptide fragment SLSLSP (SEQ ID NO: 3), in which the top graph is a chromatogram detected by a UV at 215 nm and the bottom graph is a base peak chromatogram.

The native humanized PM-1 antibody corresponding to the antibody subtype of the present invention is an antibody in which the complementarity determining region (CDR) in the variable region (V region) constituting the heavy chain (H chain) and the light chain (L chain) of a mouse monoclonal antibody termed PM-1 against IL-6R has been replaced with the corresponding CDR region of the human antibody V region. The amino acid sequence of the CDR of the L chain V region of the above mouse anti-IL-6R antibody is described in CDR 1, CDR 2 and CDR 3 on the line of L$_v$PM-1 in Table 2 of International Patent Application WO 92/19759, and the amino acid sequence of the CDR of the H chain V region of the above mouse anti-IL-6R antibody is described in CDR 1, CDR 2 and CDR 3 on the line of H$_v$PM-1 in Table 3 of International Patent Application WO 92/19759.

The framework region (FR) of the L chain V region of the above humanized PM-1 antibody is preferably derived from a human antibody REI, and the amino acid sequence is described in the FR1, FR2, FR3 and FR4 on the line of REI in Table 2 of International Patent Application WO 92/19759. Also, the framework region (FR) of the H chain V region of the above humanized PM-1 antibody is preferably derived from a human antibody NEW, and the amino acid sequence is described in the FR1, FR2, FR3 and FR4 on the line of NEW in Table 3 of International Patent Application WO 92/19759.

Furthermore, among the above V chains composed of the FR of a human antibody and the CDR of the mouse PM-1 antibody, the FR region may be modified in various manners to improve antigen-binding activity and neutralization activity. For example, the L chain V region is described in the FR1, FR2, FR3 and FR4 on the line of RV$_L$a and RV$_L$b in Table 2 of International Patent Application WO 92/19759 (termed version a to version b), and the H chain V region is described in the FR1, FR2, FR3 and FR4 on the line of RV$_H$a to RV$_H$f in Table 3 of International Patent Application WO 92/19759 (termed version a to version f).

The L chain of the humanized PM-1 antibody is composed of the L chain V region mentioned above and the constant region (C region) of a human antibody L chain, and the H chain of the humanized PM-1 antibody is composed of the H chain V region mentioned above and the constant region (C region) of a human antibody H chain. As the C region constituting the L chain, human γ-IC region is preferred, and as the C region constituting the H chain, human κC region is preferred.

Glutamine, an N-terminal amino acid of a monoclonal antibody, is known to be pyroglutamylated, and in the subtypes 1 and 2 of the humanized PM-1 antibody of the present invention the N-terminal glutamine of the heavy chain may be pyroglutamylated. Thus the subtypes 1 and 2 of the humanized PM-1 antibody of the present invention may be antibody subtypes in which the N-terminal glutamine (Gln) of the heavy chain is pyroglutamic acid (pGlu).

As the L chain and the H chain of the thus constructed humanized PM-1 antibody, as described above, there are various versions present by the modification of the FR region, and as a preferred example, there can be mentioned a H chain having the amino acid sequence set forth in SEQ ID NO: 1 and a L chain having the amino acid sequence set forth in SEQ ID NO: 2.

Incidentally, *Escherichia coli* (*E. coli*) DH5 α pPM-k3 containing a plasmid pPM-k3 comprising DNA encoding the L chain V region of the monoclonal antibody PM-1 has been internationally deposited as NCIMB 40366 and *E. coli* DH5 αpPM-h1 containing a plasmid pPM-h1 comprising DNA encoding the H chain V region of the monoclonal antibody PM-1 has been internationally deposited as NCIMB 40362, under the provisions of the Budapest Treaty on Feb. 12, 1991, with the National Collections of Industrial and Marine Bacteria Limited (Ferguson Building, Craibstone Estate, Bucksburn, Aberdeen AB 21 9YA, United Kingdom). The hybridoma PM1 producing the monoclonal antibody PM-1 has been internationally deposited as FERM BP-2998 under the provisions of the Budapest Treaty on Jul. 12, 1989 with the Patent Microorganism Depository of the National Institute of Industrial Science and Technology (Chuo 6, 1-1, Higashi 1-chome, Tsukuba city, Ibaraki pref., Japan).

DNA encoding the L chain or the H chain having the amino acid sequence as described above may be constructed according to a standard method. Specifically, a DNA sequence which was designed to ligate the CDR of a mouse antibody with the framework region (FR) of a human antibody is synthesized by the PCR method from several divided oligonucleotides having sections overlapping with one another at the ends thereof. The DNA thus obtained is ligated to a DNA encoding the C region of a human antibody and then is integrated into an expression vector, which is introduced into a host for antibody production (see European Patent Application EP 239400 and International Patent Publication WO 92-19759).

For the FR of a human antibody ligated through CDR, those in which the complementarity determining region that forms a favorable antigen binding site are selected. When desired, amino acids in the framework region of the antibody variable region may be substituted so that the complementarity determining region of a reshaped human antibody may form an appropriate antigen biding site (Sato, K. et al., Cancer Res. (1993) 53, 851-856).

For humanized antibody, the C region of a human antibody is used. As the C region of a human antibody, there can be mentioned Cγ, and Cγ1, Cγ2, Cγ3, and Cγ4, for example, can be used.

Antibody genes constructed as described above may be expressed and obtained in a known method. In the case of mammalian cells, expression may be accomplished using a vector containing a commonly used useful promoter, the antibody gene to be expressed, DNA in which the poly A signal has been operably linked at 3' downstream thereof or a vector containing said DNA. Examples of the promoter/enhancer include human cytomegalovirus immediate early promoter/enhancer.

Additionally, as the promoter/enhancer which can be used for expression of antibody for use in the present invention, there can be used viral promoters/enhancers such as retrovirus, polyoma virus, adenovirus, and simian virus 40 (SV40), and promoters/enhancers derived from mammalian cells such as human elongation factor 1α (HEF1α).

For example, expression may be readily accomplished by the method of Mulligan et al. (Mulligan, R. C. et al., Nature (1979) 277, 108-114) when SV40 promoter/enhancer is used, or by the method of Mizushima et al. (Mizushima, S. and Nagata, S., Nucleic Acids Res. (1990) 18, 5322) when HEF1α promoter/enhancer is used.

In the case of *E. coli*, expression may be conducted by operably linking a commonly used useful promoter, a signal sequence for antibody secretion, and the antibody gene to be expressed, followed by expression thereof. As the promoter, for example, there can be mentioned lacZ promoter and araB promoter. The method of Ward et al. (Ward, E. S. et al., Nature (1989) 341, 544-546; Ward, E. S. et al., FASEB J. (1992) 6, 2422-2427) may be used when lacz promoter is used, and the method of Better et al. (Better, M. et al., Science (1988) 240, 1041-1043) may be used when araB promoter is used.

As the signal sequence for antibody secretion, when produced in the periplasm of *E. coli*, the pelB signal sequence (Lei, S. P. et al., J. Bacteriol. (1987) 169, 4379-4383) can be used. After separating the antibody produced in the periplasm, the structure of the antibody is appropriately refolded before use (see, for example, WO 96/30394).

As the origin of replication, there can be used those derived from SV40, polyoma virus, adenovirus, bovine papilloma virus (BPV) and the like. Furthermore, for the amplification of the gene copy number in the host cell system, expression vectors can include, as selectable markers, the aminoglycoside phosphotransferase (APH) gene, the thymidine kinase (TK) gene, *E. coli* xanthine guanine phosphoribosyl transferase (Ecogpt) gene, the dihydrofolate reductase (dhfr) gene and the like.

For the production of antibody for use in the present invention, any production system can be used. The production system for antibody preparation comprises an in vitro or an in vivo production system. As the in vitro production system, there can be mentioned a production system which employs eukaryotic cells and a production system which employs prokaryotic cells.

When the eukaryotic cells are used, there are production systems which employ animal cells, plant cells, or fungal cells. Known animal cells include (1) mammalian cells such as CHO cells, COS cells, myeloma cells, baby hamster kidney (BHK) cells, HeLa cells, and Vero cells, (2) amphibian cells such as *Xenopus oocytes*, or (3) insect cells such as sf9, sf21, and Tn5. Known plant cells include, for example, those derived from *Nicotiana tabacum*, which may be subjected to callus culture. Known fungal cells include yeasts such as the genus *Saccharomyces*, more specifically *Saccharomyces cereviceae*, or filamentous fungi such as the genus *Aspergillus*, more specifically *Aspergillus niger*.

When the prokaryotic cells are used, there are production systems which employ bacterial cells. Known bacterial cells include *Escherichia coli* (*E. coli*), and *Bacillus subtilis*.

By introducing, via transformation, the gene of the desired antibody into these cells and culturing the transformed cells in vitro, the antibody can be obtained. Culturing is conducted in the known methods. For example, as the culture liquid, DMEM, MEM, RPMI1640, and IMDM can be used, and serum supplements such as fetal calf serum (FCS) may be used in combination. In addition, antibodies may be produced in vivo by implanting cells, into which the antibody gene has been introduced, into the abdominal cavity of an animal and the like.

As in vivo production systems, there can be mentioned those which employ animals and those which employ plants. When animals are used, there are the production systems which employ mammals and insects.

As mammals, goats, pigs, sheep, mice, and cattle can be used (Vicki Glaser, SPECTRUM Biotechnology Applications, 1993). Also as insects, silkworms can be used. When plants are used, tobacco, for example, can be used.

Antibody genes are introduced into these animals or plants, and the antibodies are produced in such animals or plants and recovered. For example, an antibody gene is inserted into the middle of the gene encoding protein which is inherently produced in the milk such as goat p casein to prepare a fusion gene. The DNA fragment containing the fusion gene into which the antibody gene has been inserted is injected into a goat embryo, and the embryo is introduced into a female goat. The desired antibody is obtained from the milk produced by the transgenic goat borne to the goat who received the embryo or offsprings thereof. In order to increase the amount of milk containing the desired antibody produced by the transgenic goat, hormones may be given to the transgenic goat as appropriate. (Ebert, K. M. et al., Bio/Technology (1994) 12, 699-702).

When silkworms are used, baculovirus into which the desired antibody gene has been inserted is infected to the silkworm, and the desired antibody can be obtained from the body fluid of the silkworm (Maeda, S. et al., Nature (1985) 315, 592-594). Moreover, when tobacco is used, the desired antibody gene is inserted into an expression vector for plants, for example pMON 530, and then the vector is introduced into a bacterium such as *Agrobacterium tumefaciens*. The bacterium is then infected to tobacco such as *Nicotiana tabacum* to obtain the desired antibody from the leaves of the tobacco (Julian, K. -C. Ma et al., Eur. J. Immunol. (1994) 24, 131-138).

When antibody is produced in the in vitro or the in vivo production systems, as described above, DNA encoding the heavy chain (H chain) or the light chain (L chain) of antibody may be separately integrated into an expression vector and the hosts are transformed simultaneously, or DNA encoding the H chain and the L chain may be integrated into a single expression vector, and the host is transformed therewith (see International Patent Publication WO 94-11523).

In order to produce the subtypes 1 and 2 of the humanized PM-1 antibody of the present invention, preferably cultured cells, most preferably CHO cells, of an animal may be used as the host, and cultured in a culture medium for animal cells. Also the medium preferably contains peptone, a hydrolyzate of protein, and thus there can be used peptone derived from beef, pork, soy beans, rice, fish meat etc. Generally, animal-derived peptone has a high expression activity, and the use of fish meat-derived peptone (for example, bonito) has an effect on the amount expressed. In this case, when a medium containing a mammalian peptone is used to produce the humanized PM-1 antibody, little production of the subtypes 1 and 2 is observed, and when a medium containing a fish meat-derived peptone or a vegetable peptone is used to produce the humanized PM-1 antibody, the ratio of the subtypes 1 and 2 becomes higher. Thus, in order to produce the subtypes 1 or 2 of the humanized PM-1 antibody of the present invention, preferably a cultured animal cell of the present invention, most preferably CHO cells, is used as the host, and it is cultured in a medium containing a fish meat-derived peptone or a vegetable peptone.

Antibodies produced and expressed as described above can be separated from the inside or outside of the host cell and then may be purified to homogeneity. Separation and purification of the antibody for use in the present invention may be accomplished by affinity chromatography. As the column used for such affinity chromatography, there can be mentioned Protein A column and Protein G column. Examples of the carriers used in the Protein A column are Hyper D, POROS, Sepharose F. F. and the like. Alternatively, methods for separation and purification conventionally used for proteins can be used without any limitation.

It can also be attained by chromatographies other than the above-mentioned affinity chromatography, such as commonly used chromatographies, for example, a combination of general column chromatographies such as ion exchange chromatography, hydrophobic chromatography, hydroxyapatite chromatography, gel-filtration and the like.

Furthermore, by combining, as appropriate, filtration, ultrafiltration, salting-out, dialysis and the like, the antibody for use in the present invention can be separated and purified. These chromatographies can be applied into fast protein liquid chromatography (FPLC) or high performance liquid chromatography (HPLC). Alternatively, reverse-phase HPLC can be used.

The concentration of antibody obtained in the above can be determined by the measurement of absorbance or by ELISA and the like. Thus, when absorbance measurement is employed, a sample is appropriately diluted with PBS(−) and then the absorbance is measured at 280 nm, followed by calculation with 1.35 OD as 1 mg/ml. When the ELISA method is used, measurement is conducted as follows. Thus, 100 µl of goat anti-human IgG (manufactured by TAG) diluted to 1 µg/ml in 0.1 M bicarbonate buffer, pH 9.6, is added to a 96-well plate (manufactured by Nunc), and is incubated overnight at 4° C. to immobilize the antibody. After blocking, 100 µl each of appropriately diluted antibody of the present invention or a sample containing the antibody, or 100 µl of human IgG (manufactured by CAPPEL) as the standard is added, and incubated at room temperature for 1 hour.

After washing, 100 µl of 5000-fold diluted alkaline phosphatase-labeled anti-human IgG antibody (manufactured by BIO SOURCE) is added, and incubated at room temperature for 1 hour. After washing, the substrate solution is added and incubated, followed by the measurement of absorbance at 405 nm using the MICROPLATE READER Model 3550 (manufactured by Bio-Rad) to calculate the concentration of the desired antibody.

Since the subtype of the humanized PM-1 antibody of the present invention has substantially the same antigen-binding activity as the native humanized PM-1 antibody, it can be used similarly to the native humanized PM-1 antibody for the treatment or prevention of various diseases in which IL-6 is involved. Examples of IL-6-related diseases include acute and chronic inflammatory diseases, autoimmune diseases such as nephritis, mesangial proliferative nephritis, Crohn's disease, ulcerative colitis, pancreatitis, infantile chronic arthritis or systemic juvenile idipathic arthritis, vasculitis, Kawasaki disease, rheumatoid arthritis, systemic lupus erythematosus, psoriasis, Sjogren's syndrome and adult Still's disease; neoplastic diseases such as multiple myeloma, Castleman's disease, malignant lymphoma and renal cancer; infectious diseases such as HIV infection and EBV infection; cachexia; plasmacytosis, hyperimmunoglobulin disease, anemia and the like, and preferably rheumatoid arthritis, plasmacytosis, hyperimmunoglobulin disease, anemia, nephritis, cachexia, multiple myeloma, Castleman's disease, mesangial proliferative nephritis, systemic lupus erythematosus, Crohn's disease, pancreatitis, psoriasis, and infantile chronic arthritis or systemic juvenile idipathic arthritis.

The pharmaceutical composition of the present invention may be administered, either orally or parenterally, systemically or locally. For example, intravenous injection such as drip infusion, intramuscular injection, intrapleural injection, intraperitoneal injection, subcutaneous injection, suppositories, intestinal lavage, oral enteric coated tablets, and the like can be selected, and the method of administration may be chosen, as appropriate, depending on the age and the conditions of the patient. The effective dosage is chosen from the range of 0.01 mg to 100 mg per kg of body weight per administration. Alternatively, the dosage in the range of 1 to 1000 mg, preferably 5 to 50 mg per patient may be chosen.

Preferred dosages and preferred methods of administration are such that, in the case of anti-IL-6 receptor antibody, the amounts wherein free antibody is present in the blood are effective dosages. In specific examples, 0.5 mg to 40 mg per kg of body weight, preferably 1 mg to 20 mg, per month (4 weeks) are administered in one to several divided doses, for example in the administration schedule of twice per week, once per week, once every two weeks, once every four weeks and the like by intravenous injection such as drip infusion and subcutaneous injection. The administration schedule can be adjusted by observing the disease conditions and blood levels of laboratory tests by, for example, extending the administration interval from twice per week or once per week to once per two weeks, once per three weeks, once per four weeks, and the like.

The pharmaceutical composition of the present invention may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof depending on the dosage form.

EXAMPLES

The present invention will now be explained in more detail with reference to the working examples and reference examples. It should be noted, however, that the present invention is not limited to them in any way.

Example 1

The Expression of an Antibody Composition Containing the Native Humanized PM-1 Antibody/Subtype 1/Subtype 2

Construction of Expressing Cells
(1) Preparation of Human IL-6 Receptor Antibody PM-1

Anti-IL-6R antibody MT18 prepared by the method of Hirata et al. (J. Immunol., (1989) 143:2900-2906) was bound to CNBr-activated Sepharose 4B (manufactured by Pharmacia Fine Chemicals, Piscataway, N.J.) according to the attached regimen, and IL-6R (Yamasaki, K. et al., Science (1988) 241:825-828) was purified.

Thus, a human myeloma cell line U266 was solubilized with 1 mM p-paraminophenyl methane sulfonyl fluoride hydrochloride (manufactured by Wako Chemicals) (digitonin buffer) containing 1% digitonin (manufactured by Wako Chemicals), 10 mM triethanolamine (pH 7.8) and 0.15 M NaCl, and mixed with the MT18 antibody bound to Sepharose 4B beads. Then, the beads were washed six times with the digitonin buffer to prepare the partially purified IL-6R to be used for immunization.

BALB/c mice were immunized four times every ten days with the above partially purified IL-6R obtained from $3 \times 10^9$ U266 cells, and then a hybridoma was prepared using a standard method. The culture supernatant of the hybridoma from the growth-positive well was tested for its activity of binding to IL-6R according to the method described below. $5 \times 10^7$ U266 cells were labeled with $^{35}$S-methionine (2.5 mCi) and were solubilized with the above digitonin buffer.

The solubilized U266 cells were mixed with a 0.04 ml volume of MT18 antibody bound to Sepharose 4B beads, and then were washed six times with the digitonin buffer. $^{35}$S-methionine-labeled IL-6R was eluted with 0.25 ml of the digitonin buffer (pH 3.4) and was neutralized in 0.025 ml of 1 M Tris (pH 7.4). 0.05 ml of the hybridoma culture supernatant was mixed with 0.01 ml of Protein G Sepharose (manufactured by Pharmacia).

After washing, Sepharose was incubated with 0.005 ml of $^{35}$S-labeled IL-6R solution prepared as described above. The immunoprecipitate was analyzed by SDS-PAGE to investigate the hybridoma culture supernatant that reacts with IL-6R. As a result, a reaction-positive hybridoma clone PM-1 was established. The IL-6R antibody PM-1 produced from the hybridoma PM-1 has a subtype of IgG1κ.

The inhibitory activity of the antibody produced by the hybridoma PM-1 on the binding of IL-6 to human IL-6R was studied using the human myeloma cell line U266. A human recombinant IL-6 was prepared from *E. coli* (Hirano et al., Immunol. Lett., (1988) 17:41), and was labeled with $^{125}$I using the Bolton-Hunter reagent (New England Nuclear, Boston, Mass.) (Taga, T. et al., J. Exp. Med. (1987) 166:967). $4 \times 10^5$ U266 cells were cultured together with the culture supernatant of 70% (v/v) hybridoma PM-1 and 14,000 cpm of $^{125}$I-labeled IL-6 in the presence of a 100-fold excessive amount of nonlabelled IL-6 at room temperature for 1 hour. Seventy μl of the sample was layered on 300 μl FCS in a 400 μl microfuge polyethylene tube. After centrifugation, the radioactivity of the cell was determined. The result revealed that the antibody produced by the hybridoma PM-1 inhibits the binding of IL-6 to IL-6R.

(2) Creation of Humanized Antibody hPM-1

Using a human elongation factor Iα promoter described in Example 10 of International Patent Publication WO 92/19759 and according to the method described in Reference Example 2 of Japanese Unexamined Patent Publication (Kokai) No. 8-99902, a single expression vector containing both the L chain and H chain genes was constructed, and was investigated using CHO cells that produce the humanized PM-1 antibody (anti-human IL-6 receptor antibody), said cells being prepared by inserting the expression vector into CHO cells. The ability of the humanized antibody obtained to bind to human IL-6R was confirmed by ELISA. Furthermore, hPM-1 inhibited the binding of human IL-6 to human IL-6R in a similar manner to a mouse antibody or a chimeric antibody.

Cell Culture and the Expression of Humanized PM-1 Antibody

In order to obtain a large quantity of humanized PM-1 antibody, the expressing cells were cultured in a commercially available serum-free medium and a modified medium. The culture condition was an environment suitable for the culturing of CHO cells. In order to increase the amount expressed of the desired antibody, various additives may be added to the medium. Among them, various types of peptones are widely used. Peptones derived from beef, pork, soy beans, rice, fish meat etc. are widely commercially available. The effect depends on the compatibility with the cell line. Generally, the effect of expression is high for animal-derived peptones. In the course of investigating the effect of various peptones, the use of a peptone derived from fish meat (bonito) was found to be effective for the amount expressed.

The purification of the antibody expressed was accomplished by combinations of commonly used column chromatographies, for example, affinity chromatography, ion exchange chromatography, hydrophobic chromatography, hydroxyapatite chromatography, gel-filtration and the like. In a molecular species of the humanized PM-1 antibody that was expressed by culturing CHO cells using a peptone derived from fish meat, there was observed a molecular species that was present in scarce amounts when beef-derived peptone was used. This molecular species was also seen when a vegetable-derived peptone was used.

Example 2

Analysis of the Humanized PM-1 Antibody, the Subtype 1 and the Subtype 2

Materials and Methods

As the materials, the native humanized PM-1 antibody (sometimes referred to as Main), the subtypes 1 and 2 of said antibody, and, as the reference peptides, a peptide Ser-Leu-Ser-Leu-Ser-Pro (SLSLSP) (SEQ ID NO: 3) that is present at the C-terminal of the humanized PM-1 antibody and in which Gly at the C-terminal has been removed and a peptide SLSLSP-NH$_2$ (SEQ ID NO: 4) in which the C-terminal Pro has been amidated were used. The peptide SLSLSP (SEQ ID NO: 3) and the amidated peptide SLSLSP-NH$_2$ (SEQ ID NO: 4) were chemically synthesized. The humanized PM-1 antibody Main and the subtypes 1 and 2 of said antibody were obtained by subjecting the humanized PM-1 antibody obtained in Example 1 to a column chromatography and collecting and purifying it by the following method.

The column used was the Poly CAT A (100×4.6 mm) manufactured by Poly LC, and the guard column used was the Poly CAT A Javelin guard (10×4.0 mm) manufactured by Poly LC. The mobile phases used were the mobile phase A (25 mM 2-[N-morpholino]ethanesulfonic acid buffer, pH 6.1, containing 0.05% NaN$_3$) and the mobile phase B (25 mM 2-[N-morpholino]ethanesulfonic acid buffer, pH 6.1, containing 250 mM sodium acetate and 0.05% NaN$_3$). As the gradient condition, the ratio of the mobile phase B was 0 min/35%, 5 min/35%, 59 min/60%, and 60 min/100%. The flow rate was 1 ml/min and detected by UV/VIS absorbance at 280 nm.

The Enzymatic Digestion of the Humanized PM-1 Antibody Main, the Subtype 1 and the Subtype 2

200 μg equivalents of the humanized PM-1 antibody Main, the subtype 1 and the subtype 2 were placed in a simple ultrafiltration cartridge (Minicent, manufactured by Toso), into which a denaturant solution (100 mM 2-amino-2-hydroxymethyl-1,3-propanediol-hydrochloric acid buffer, pH 8.3, containing 7 M guanidine and 1 mM ethylenediaminetetraacetic acid) was added to a liquid volume of 500 μl. The cartridge was centrifuged at 5° C. to a liquid volume of about 50 μl. The sample was collected into a microtube, to which a denaturant solution (the same composition as above) was added to make a total volume of 300 μl.

To each solution, 50 μl of a DTT solution (a denaturant solution containing 162 mM dithiothreitol) was added and the head space was replaced with N$_2$, and allowed to stand in an incubating block at 37° C. for 1 hour. Furthermore, 45 μl of the IAA solution (0.2 N sodium hydroxide solution containing 417 mM iodoacetic acid) was added and allowed to stand in the dark at 37° C. for 30 minutes. The reaction mixture was recovered, and each sample was dialyzed, using dialysis tubing, against 500 ml of the Tris-HCl buffer (100 mM 2-amino-2-hydroxymethyl-1,3-propanediol-hydrochloric acid buffer, pH 8.0, containing 2 M urea) at 5° C. for 20 hours (dialysis membrane: M.W.=8000, manufactured by Spectrum). The dialyzed samples were recovered and to each of them, 20 μl of the trypsin solution (trypsin is dissolved in the Tris-HCl buffer (the same composition as above) to make 250 ng/μl) was added and allowed to stand at 37° C. for 16 hours.

Analysis of the Trypsin Digests and the Reference Peptides

Forty μl of each sample treated as above was subjected to the liquid chromatography-mass spectrometry (LC-MS/MS). For the reference peptide solutions, i.e, the SLSLSP (SEQ ID NO: 3) solution (SLSLSP (SEQ ID NO: 3) is dissolved in water to make 4 μM) and the SLSLSP-NH$_2$ (SEQ ID NO: 4) solution (SLSLSP-NH$_2$ (SEQ ID NO: 4) is dissolved in water to make 4 μM), 50 μl is subjected to the liquid chromatography-mass spectrometry.

The condition for the liquid chromatography-mass spectrometry was as follows. Thus, the column used was the YMC-Pack ODS (250×2.0 mm, 5 μm, 300 Angstrom) manufactured by YMC. The mobile phase used was the mobile phase A (5% acetonitrile solution containing 0.1% trifluoroacetic acid) and the mobile phase B (95% acetonitrile solution containing 0.1% trifluoroacetic acid). As the gradient condition, the ratio of the mobile phase B was 0 min/0%, 10 min/0%, 120 min/35%, and 140 min/35%. The flow rate was 0.2 ml/min and detection was by UV/VIS absorbance at 215 nm.

Result of Analysis of the Trypsin Digests and the Reference Peptides (1) Measurement of the Reference Peptide Fragments (a) Measurement of the Peptide Fragment SLSLSP (SEQ ID NO: 3)

Figure 2:
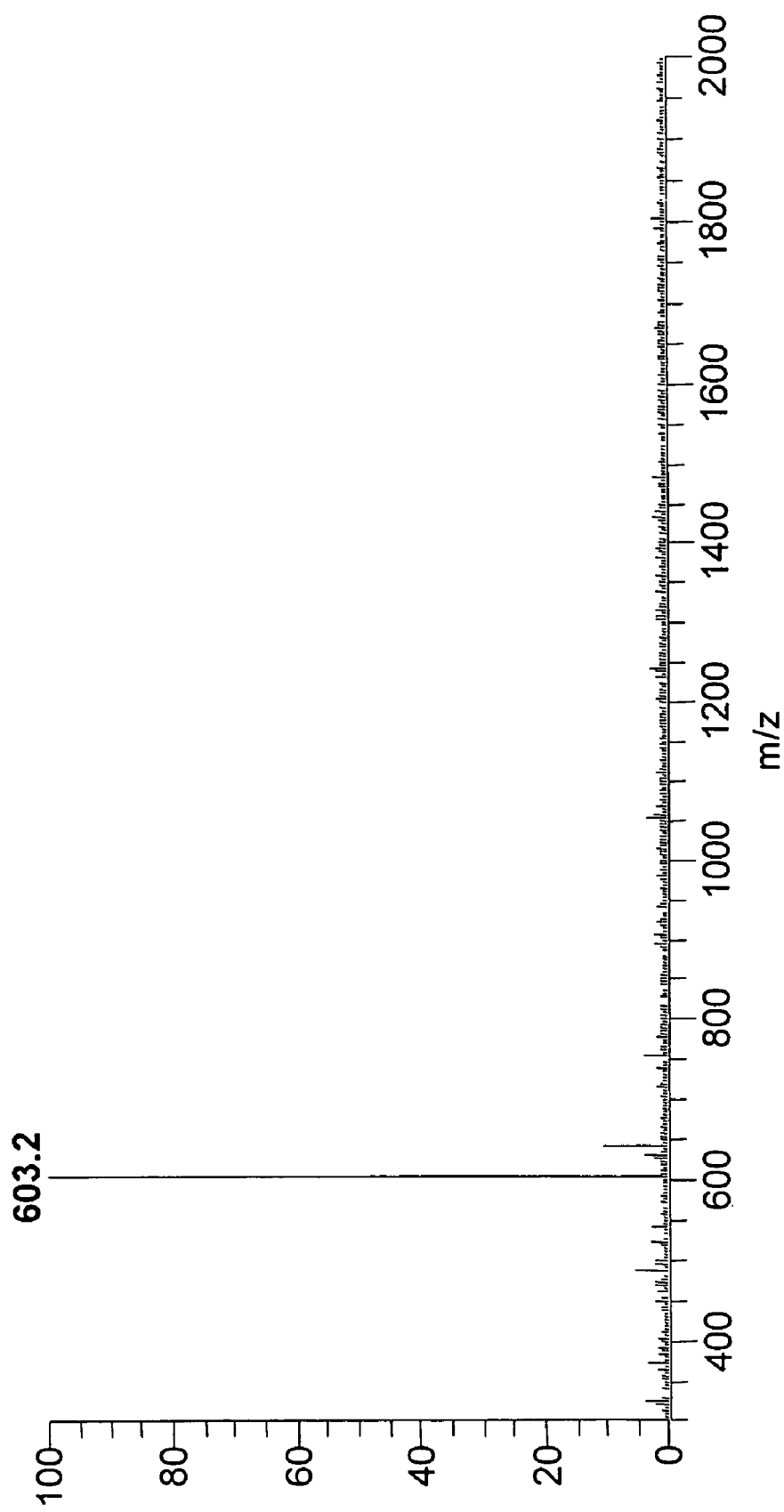
FIG. 2 shows a mass spectrum in the liquid chromatography (LC)-mass spectrometry (MS) of the peptide fragment SLSLSP (SEQ ID NO: 3).
Figure 3:
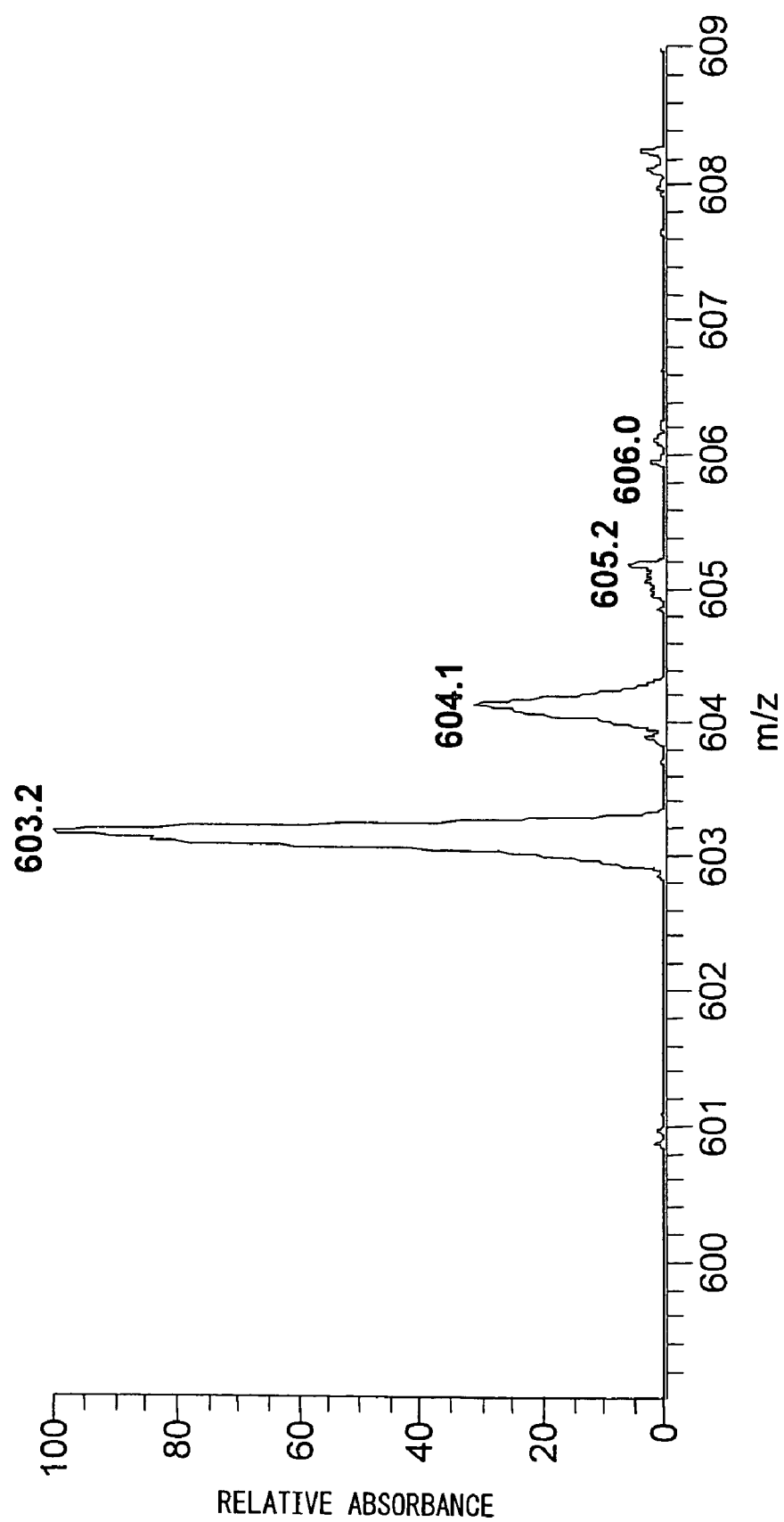
FIG. 3 shows a zoom scan spectrum in the liquid chromatography (LC)-mass spectrometry (MS) of the peptide fragment SLSLSP (SEQ ID NO: 3).

FIG. 1 to FIG. 3 show the result of liquid chromatography (LC)-mass spectrometry (MS) of the peptide fragment SLSLSP (SEQ ID NO: 3). The top of FIG. 1 shows a chromatogram detected with a UV at 215 nm, and the bottom shows a chromatogram of a base peak chromatogram. FIG. 2 shows a mass spectrum, and FIG. 3 shows a zoom scan spectrum. The molecular weight (602.2) obtained was in close agreement with the theoretical value (602.3; monoisotopic molecular weight) (FIG. 2 and FIG. 3).

(b) Measurement of the Peptide Fragment SLSLSP-NH$_2$ (SEQ ID NO: 4)

Figure 4:
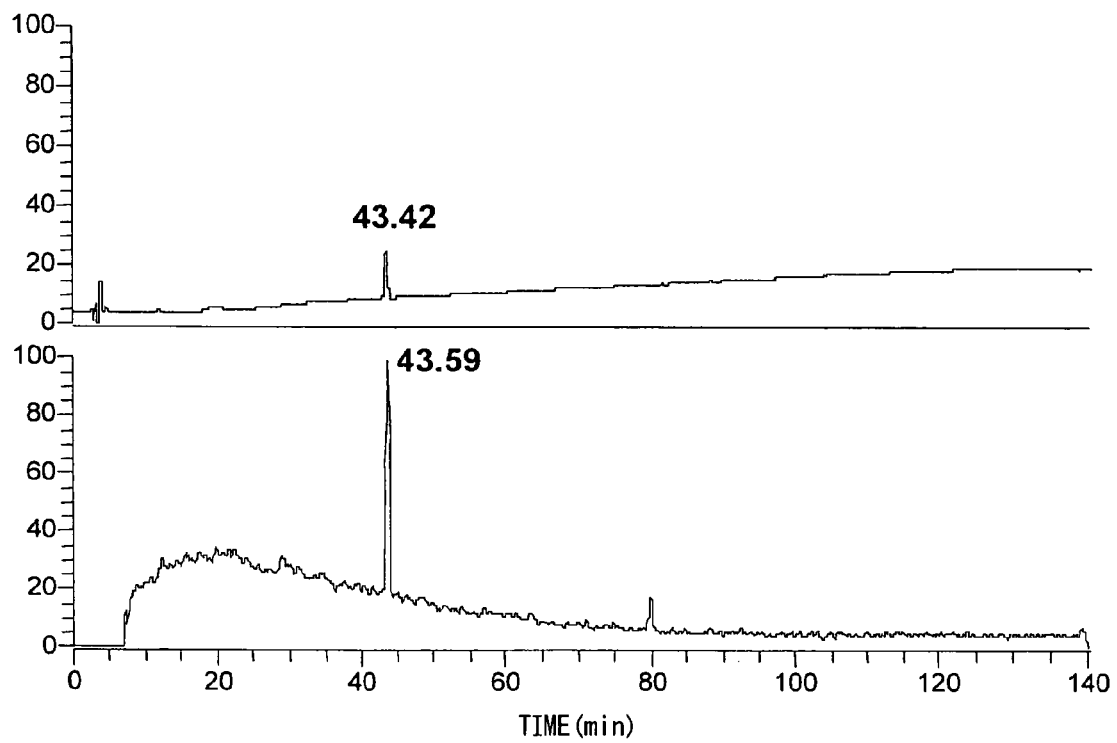
FIG. 4 shows the result of liquid chromatography in the liquid chromatography (LC)-mass spectrometry (MS) of the peptide fragment SLSLSP-NH$_2$ (SEQ ID NO: 4), in which the top graph is a chromatogram detected by a UV at 215 nm and the bottom graph is a base peak chromatogram.
Figure 5:
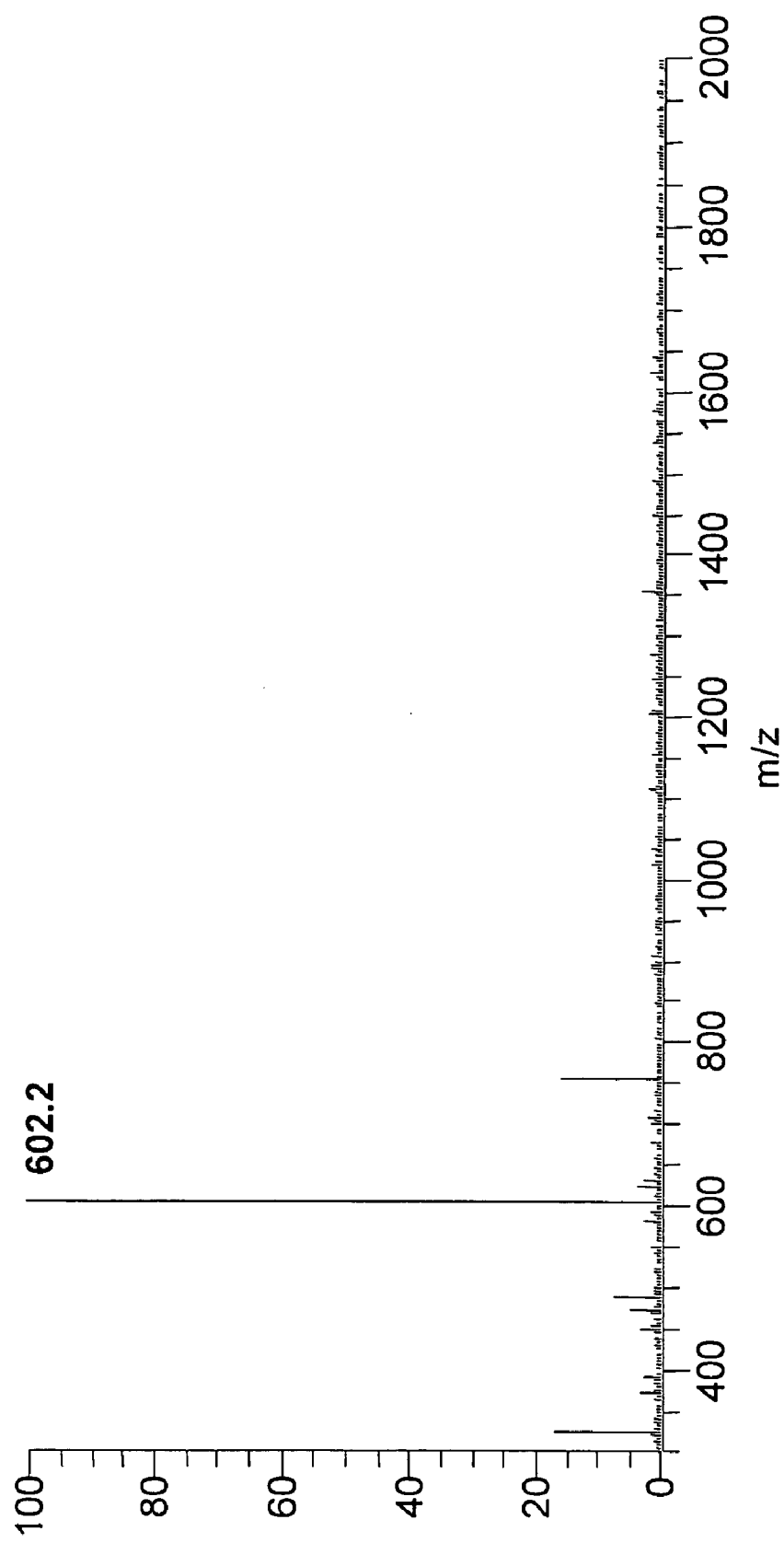
FIG. 5 shows a mass spectrum in the liquid chromatography (LC)-mass spectrometry (MS) of the peptide fragment SLSLSP-NH$_2$ (SEQ ID NO: 4).
Figure 6:
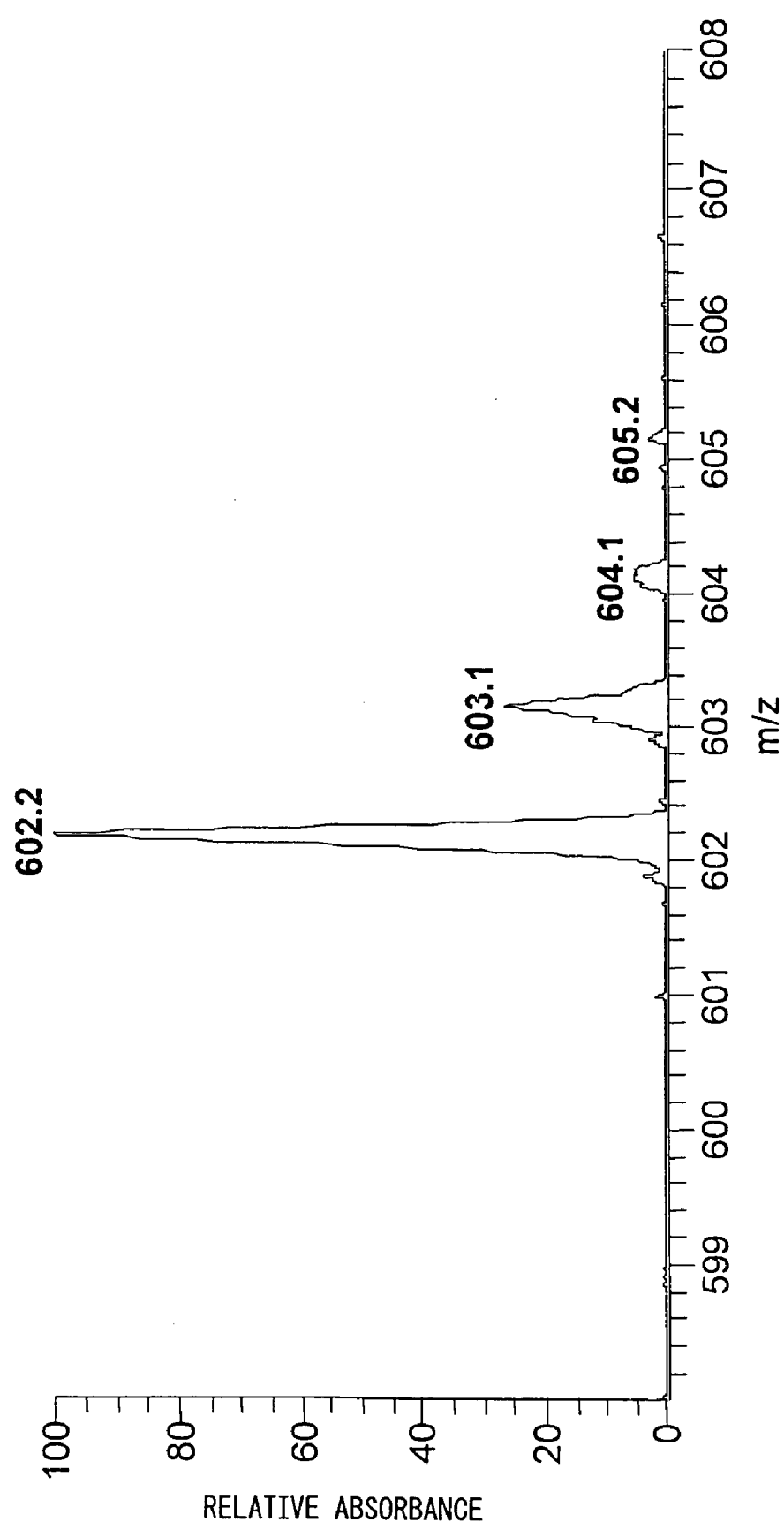
FIG. 6 shows a zoom scan spectrum in the liquid chromatography (LC)-mass spectrometry (MS) of the peptide fragment SLSLSP-NH$_2$ (SEQ ID NO: 4).

FIG. 4 to FIG. 6 show the result of liquid chromatography (LC)-mass spectrometry (MS) of the peptide fragment SLSLSP (SEQ ID NO: 3). The top of FIG. 4 shows a chromatogram detected with a UV at 215 nm, and the bottom shows a chromatogram of a base peak chromatogram. FIG. 5 shows a mass spectrum, and FIG. 6 shows a zoom scan spectrum. The molecular weight (601.2) obtained was in close agreement with the theoretical value (601.3; monoisotopic molecular weight) (FIG. 5 and FIG. 6).

(c) Measurement of the Mixture of the Peptide Fragments SLSLSP (SEQ ID NO: 3) and SLSLSP-NH$_2$ (SEQ ID NO: 4)

Figure 7:
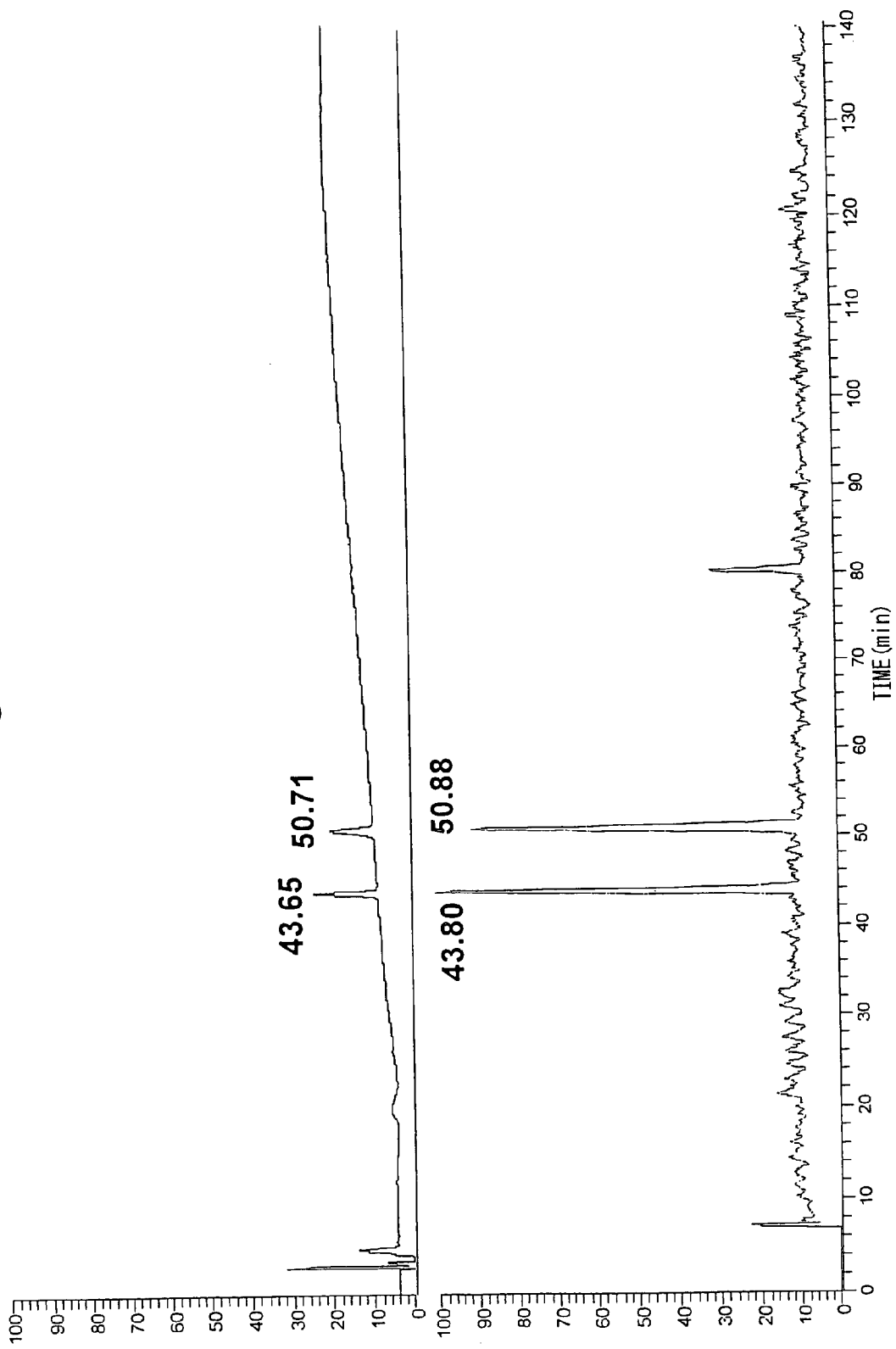
FIG. 7 shows the result of liquid chromatography in the liquid chromatography (LC)-mass spectrometry (MS) of the mixture of the peptide fragments SLSLSP (SEQ ID NO: 3) and SLSLSP-NH$_2$ (SEQ ID NO: 4), in which the top graph is a chromatogam detected by a UV at 215 nm and the bottom graph is a base peak chromatogram.
Figure 8:
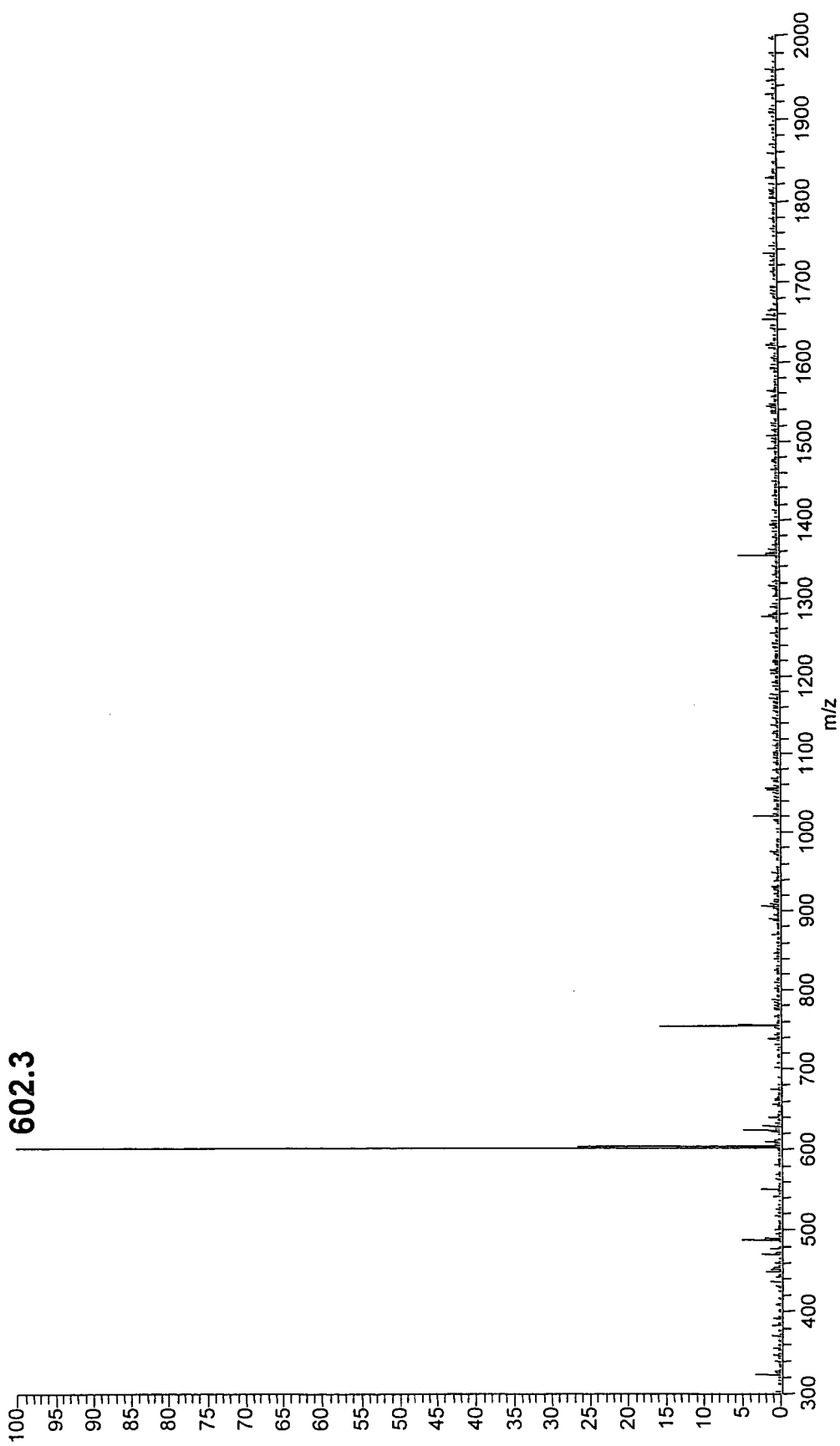
FIG. 8 shows a mass spectrum of the peak at a retention time of 44 minutes in FIG. 7.
Figure 9:
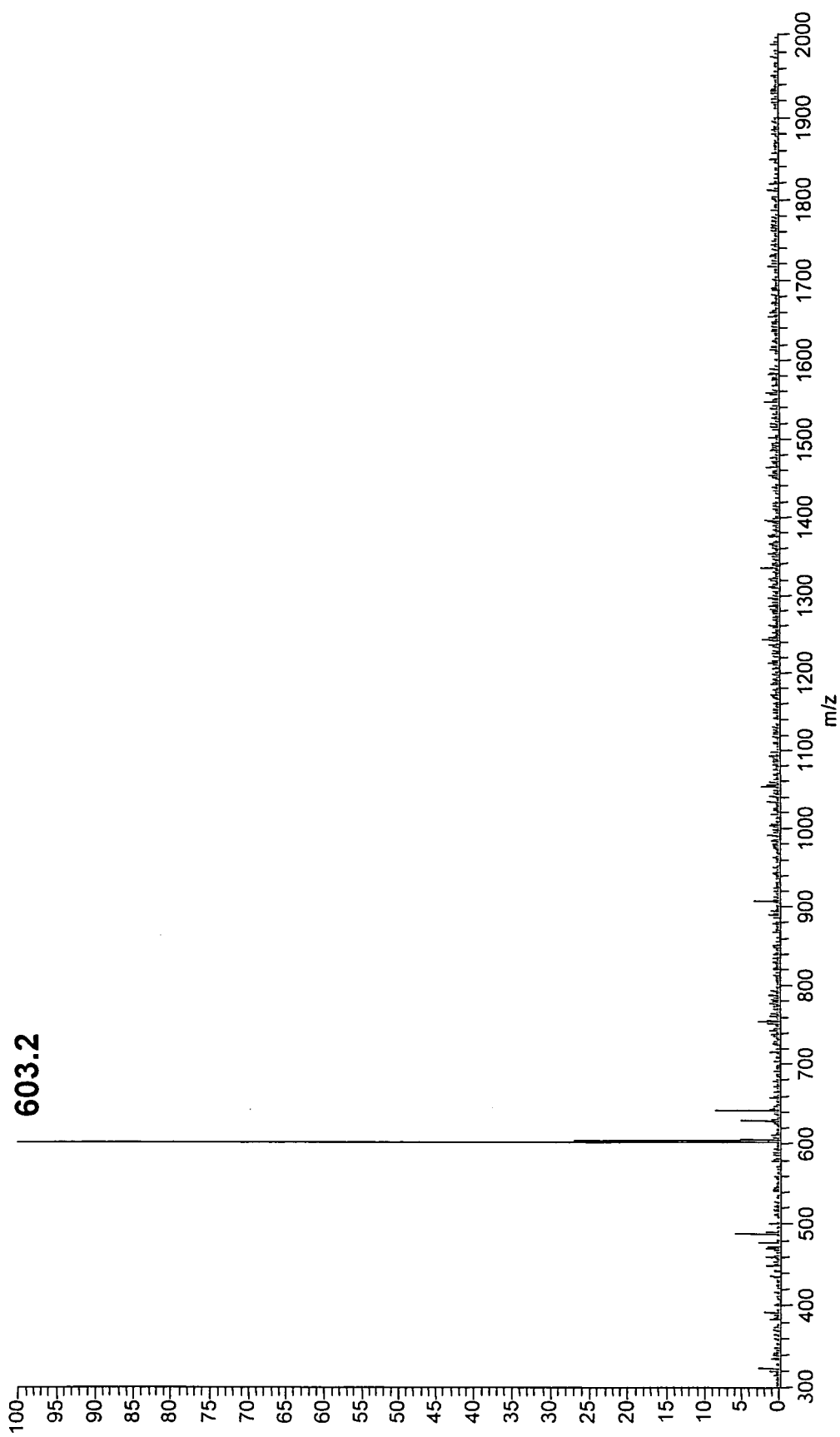
FIG. 9 shows a mass spectrum of the peak at a retention time of 51 minutes in FIG. 7.

FIG. 7 to FIG. 9 show the result of liquid chromatography (LC)-mass spectrometry (MS) of the mixture of the peptide fragment SLSLSP (SEQ ID NO: 3) and SLSLSP-NH$_2$ (SEQ ID NO: 4). The top of FIG. 7 shows a chromatogram detected with a UV at 215 nm, and the bottom shows a chromatogram of a base peak chromatogram. FIG. 8 shows the mass spectrum of a peak at a retention time of 44 minutes in FIG. 7, and FIG. 9 shows the mass spectrum of a peak at a retention time of 51 minutes in FIG. 7. The both peptide fragments were completely separated under the condition of the above liquid chromatography.

(2) Analysis of the Structure of the H Chain C-Terminal of the Humanized PM-1 Antibody (a) Analysis of the Structure of the H Chain C-Terminal of the Humanized PM-1 Antibody (Main)

Figure 10:
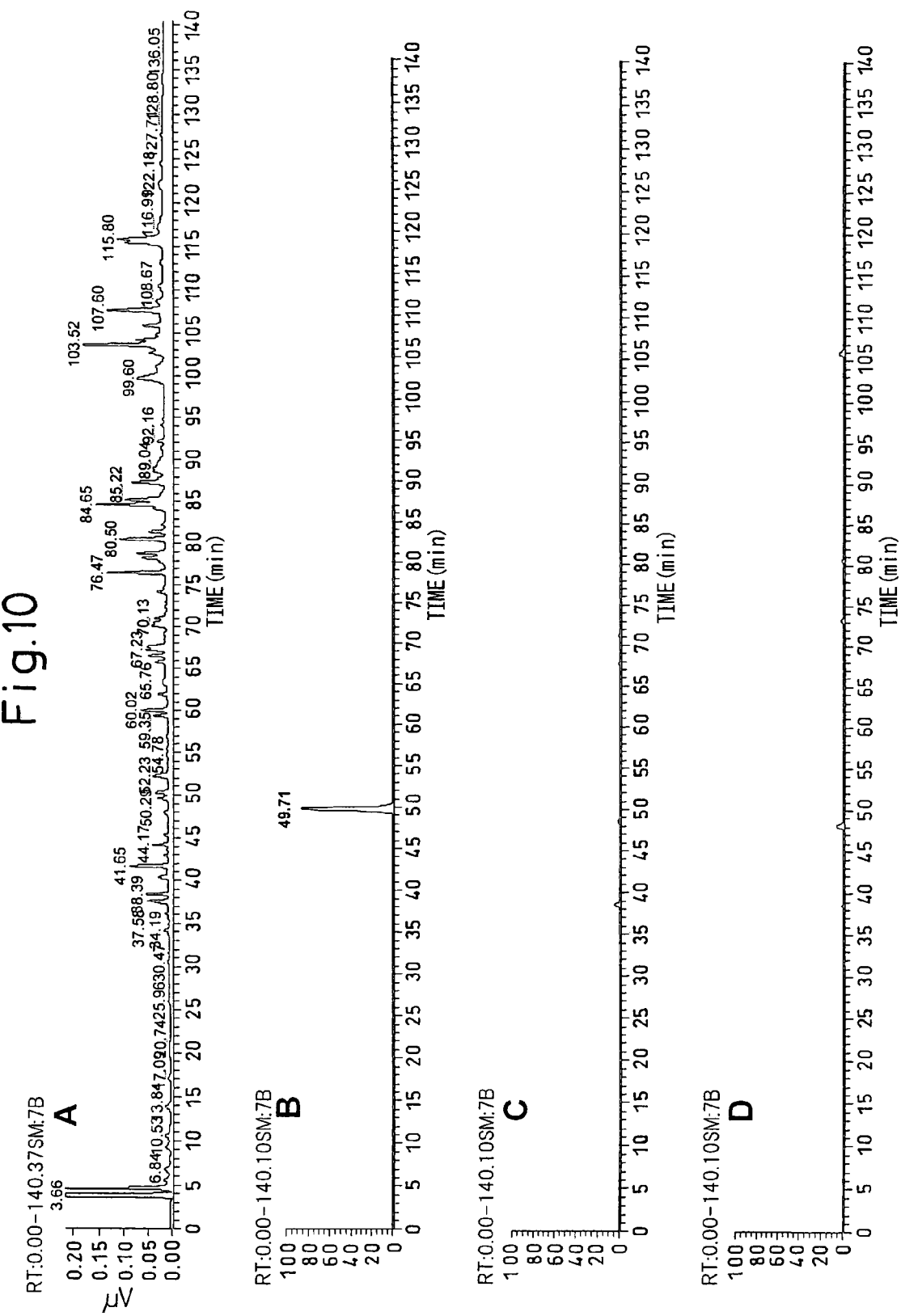
FIG. 10A shows a peptide map of peptides obtained by the reduction/carboxymethylation of the humanized PM-1 antibody (Main) followed by trypsin digestion.
FIG. 10B shows the MS chromatogram of molecular weight of SLSLSPG (SEQ ID NO: 5) (selective monitoring at m/z 660.3±0.5)
FIG. 10C shows that of SLSLSP-NH$_2$ (SEQ ID NO: 4) (selective monitoring at m/z 602.3±0.5)
FIG. 10D shows that of SLSLSP (SEQ ID NO: 3) (selective monitoring at m/z 603.3±0.5).

FIG. 10A shows a peptide map of peptides obtained by the reduction/carboxymethylation of the humanized PM-1 antibody (Main) followed by trypsin digestion. In order to investigate the structure of the C-terminal fragment of the H chain, the MS chromatogram of SLSLSPG (SEQ ID NO: 5) (selective monitoring at m/z 660.3±0.5) is shown in FIG. 10B, that of SLSLSP-NH$_2$ (SEQ ID NO: 4) (selective monitoring at m/z 602.3±0.5) in FIG. 10C, and that of SLSLSP (SEQ ID NO: 4) (selective monitoring at m/z 603.3±0.5) in FIG. 10D. A peak corresponding to SLSLSPG (SEQ ID NO: 5) was detected at 49.7 minutes, but no peptide fragments having the molecular weight of SLSLSP-NH$_2$ (SEQ ID NO: 4) and SLSLSP (SEQ ID NO: 3) were found.

Figure 11:
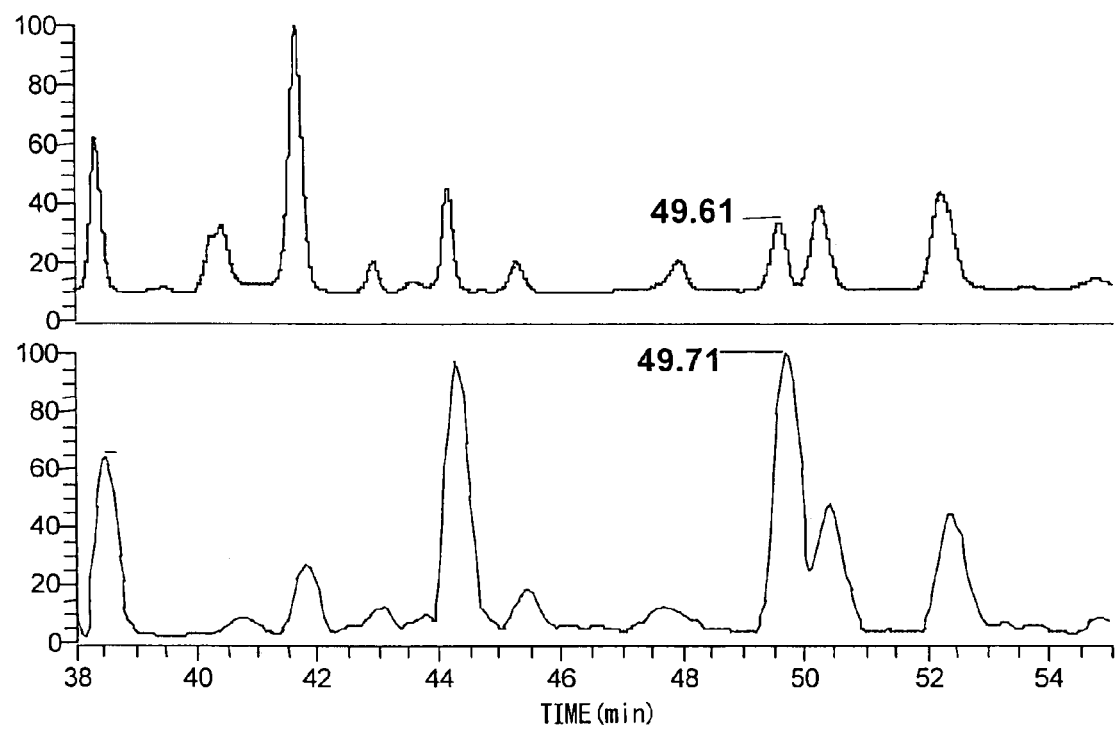
FIG. 11 shows the result of LC-MS/MS analysis of a peptide obtained by the reduction/carboxymethylation of the humanized PM-1 antibody (Main) followed by trypsin digestion, in which the top is a chromatogram detected by a UV at 215 nm and the bottom is a base peak chromatogram.
Figure 12:
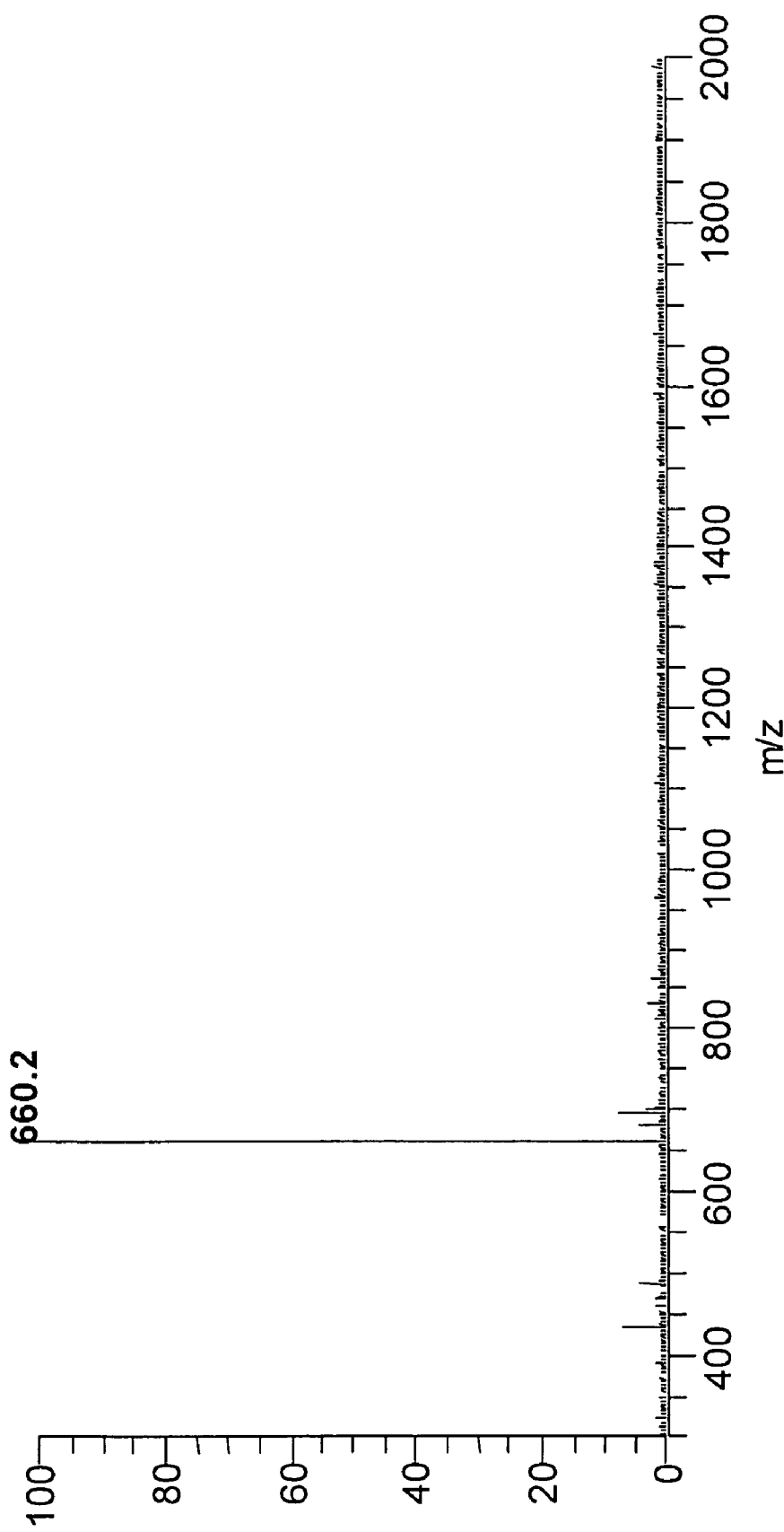
FIG. 12 shows a mass spectrum of the peak at a retention time of 50 minutes in FIG. 11.
Figure 13:
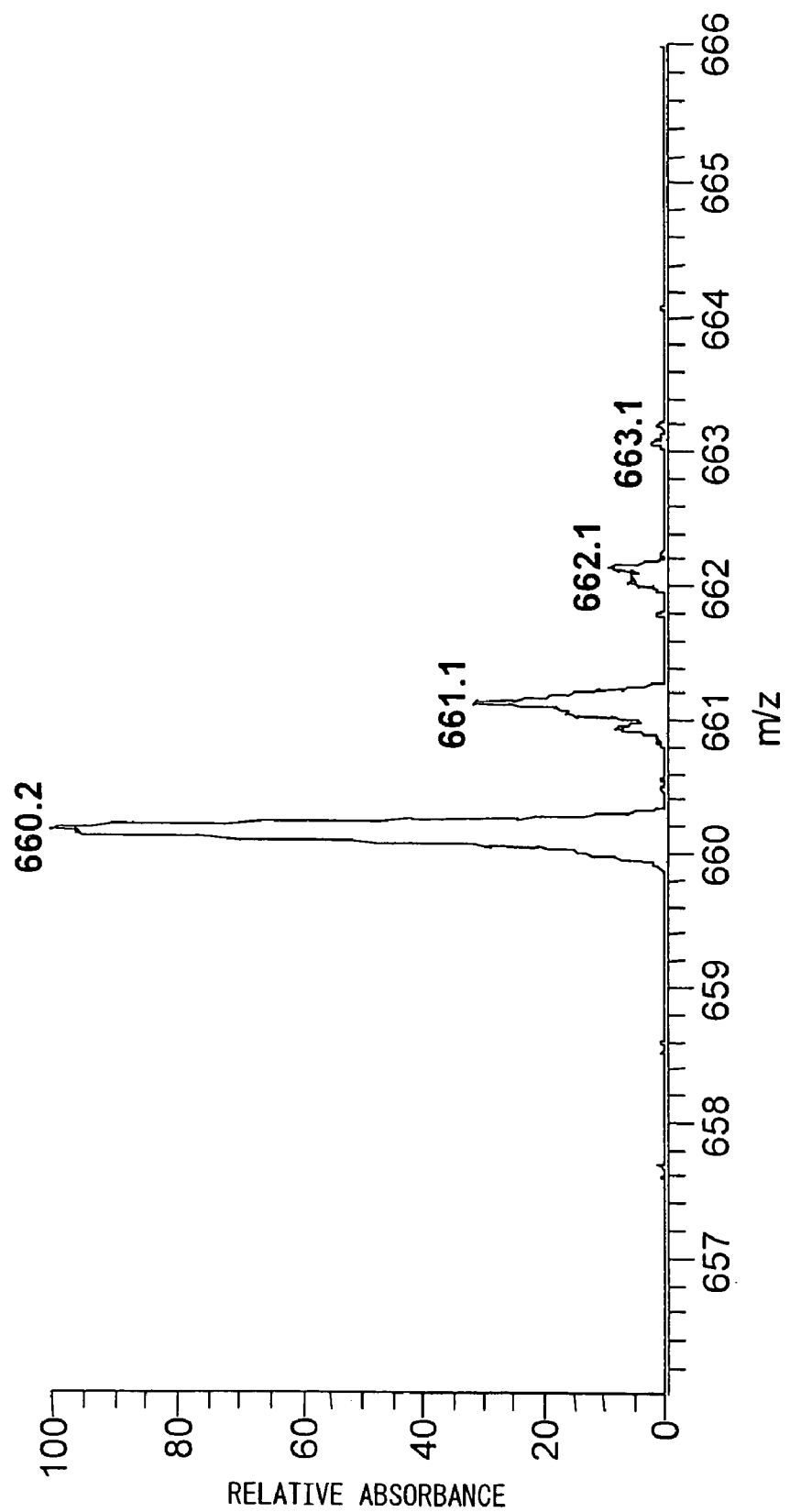
FIG. 13 shows a zoom scan spectrum of the same peak as in FIG. 11.

FIG. 11 to FIG. 13 show the result of LC-MS/MS analysis of a peptide obtained by the reduction/carboxymethylation of the humanized PM-1 antibody (Main) followed by trypsin digestion. The top in FIG. 11 shows a chromatogram detected by a UV at 215 nm and the bottom shows a base peak chromatogram. FIG. 12 shows a mass spectrum of the peak at a retention time of 50 minutes in FIG. 11, and FIG. 13 shows a zoom scan spectrum of the same peak as in FIG. 11. From these results, the detected peak was shown to have the amino acid sequence SLSLSPG (SEQ ID NO: 5). Thus, it was demonstrated that both C-terminals of the H chain of the humanized PM-1 antibody (Main) have the -SLSLSPG (SEQ ID NO: 5) sequence.

(b) Analysis of the Structure of the H Chain C-Terminal of the Humanized PM-1 Antibody Subtype 1

Figure 14:
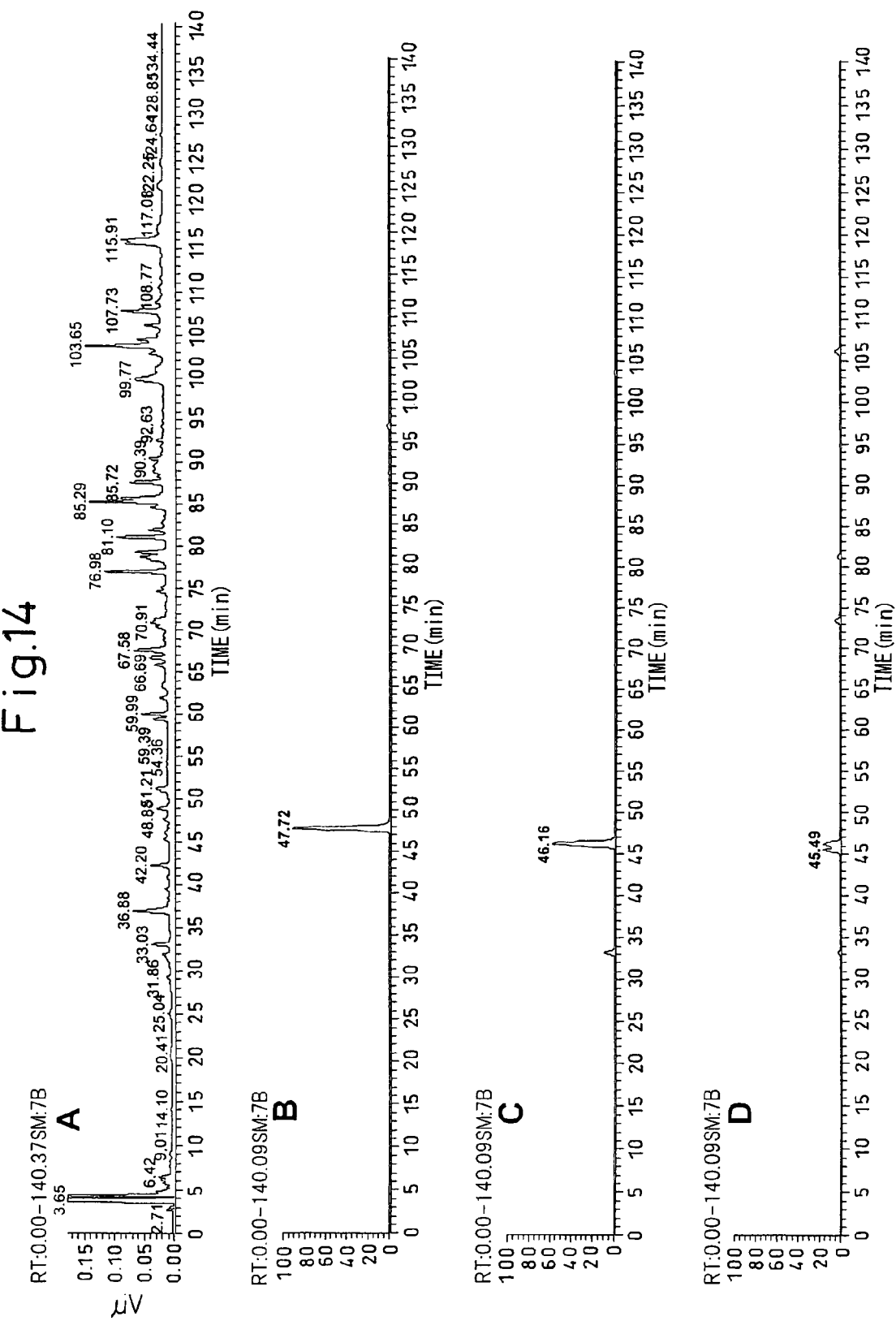
FIG. 14A shows a peptide map of peptides obtained by the reduction/carboxymethylation of the humanized PM-1 antibody subtype 1 followed by trypsin digestion.
FIG. 14B shows the MS chromatogram of molecular weight of SLSLSPG (SEQ ID NO: 5) (selective monitoring at m/z 660.3±0.5)
FIG. 14C shows that of SLSLSP-NH$_2$ (SEQ ID NO: 4) (selective monitoring at m/z 602.3±0.5)
FIG. 14D shows that of SLSLSP (SEQ ID NO: 3) (selective monitoring at m/z 603.3±0.5).

FIG. 14A shows a peptide map of peptides obtained by the reduction/carboxymethylation of the humanized PM-1 antibody subtype 1 followed by trypsin digestion. In order to investigate the structure of the C-terminal fragment of the H chain, FIG. 14B shows the MS chromatogram of molecular weight of SLSLSPG (SEQ ID NO: 5) (selective monitoring at m/z 660.3±0.5). FIG. 14 C shows that of SLSLSP-NH$_2$ (SEQ ID NO: 4) (selective monitoring at m/z 602.3±0.5), and FIG. 14D shows that of SLSLSP (SEQ ID NO: 3) (selective monitoring at m/z 603.3±0.5). In addition to a peak corresponding to SLSLSPG (SEQ ID NO: 5) at 47.7 minutes, a peak corresponding to SLSLSP-NH$_2$ (SEQ ID NO: 4) at 46.2 minutes was noted (though a peak with a molecular weight of 603.3 was noted at about 46 minutes in FIG. 14D, it is not SLSLSP (SEQ ID NO: 3), based on the retention time).

Figure 15:
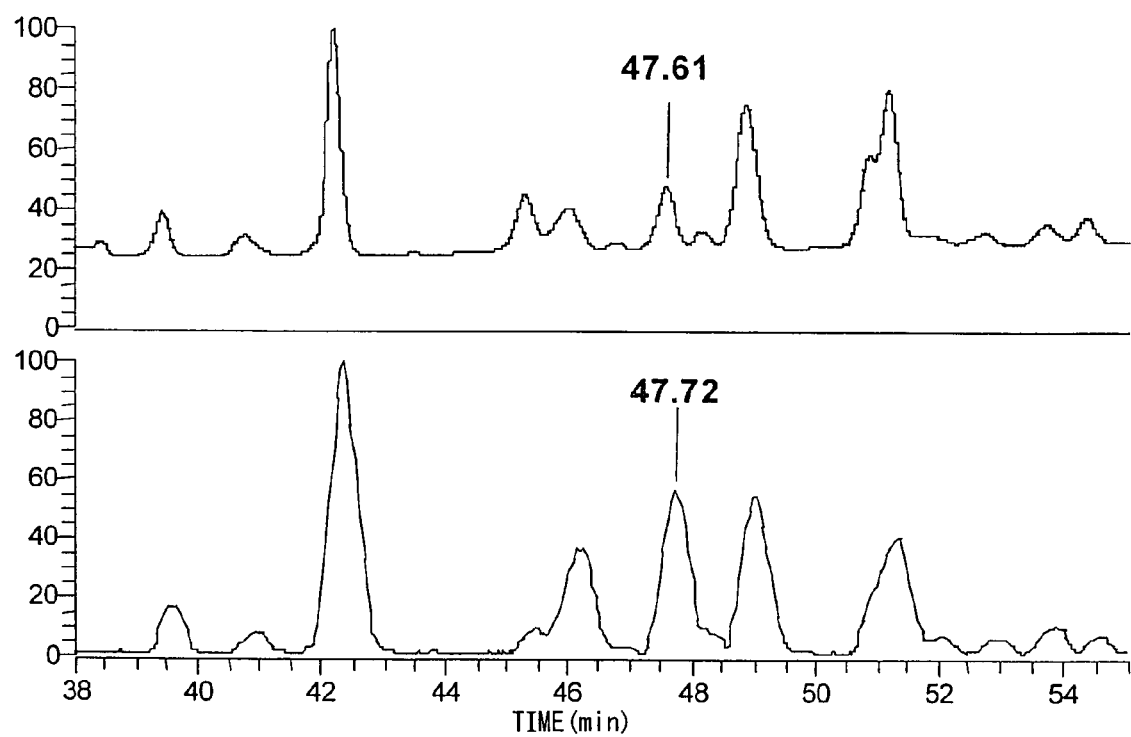
FIG. 15 shows the result (on the peak in FIG. 17B) of liquid chromatography in the LC-MS/MS analysis of a peptide obtained by the reduction/carboxymethylation of the humanized PM-1 antibody subtype 1 followed by trypsin digestion, in which the top is a chromatogram detected by a UV at 215 nm and the bottom is a base peak chromatogram.
Figure 16:
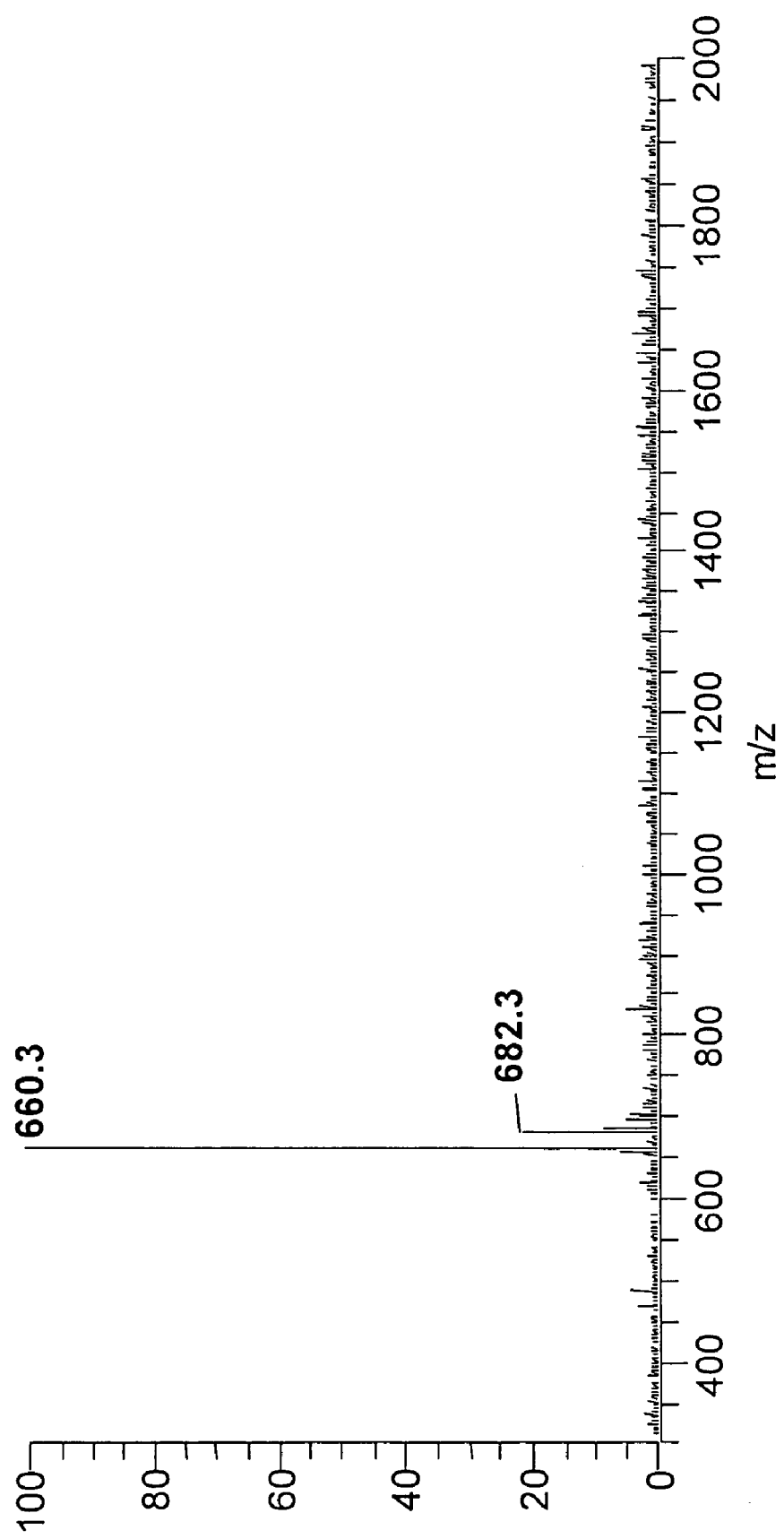
FIG. 16 shows a mass spectrum of the peak at a retention time of 48 minutes in FIG. 15.
Figure 17:
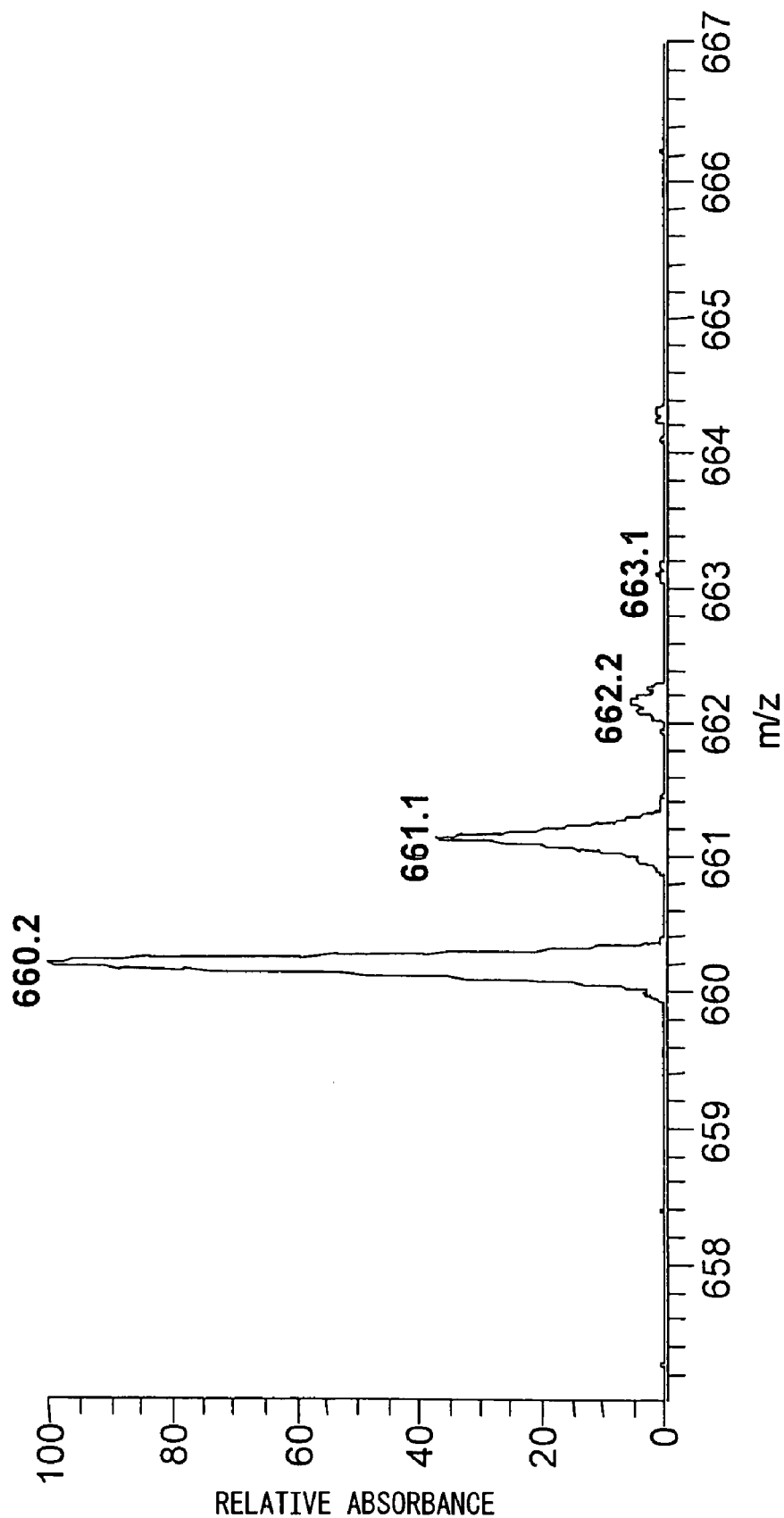
FIG. 17 shows a zoom scan spectrum of the same peak as in FIG. 16.

FIG. 15 to FIG. 17 show the result (on the peak in FIG. 14B) of LC-MS/MS analysis of a peptide obtained by the reduction/carboxymethylation of the humanized PM-1 antibody subtype 1 followed by trypsin digestion. In FIG. 15, the top is a chromatogram detected by a UV at 215 nm and the bottom is a base peak chromatogram. FIG. 16 shows a mass spectrum of the peak at a retention time of 48 minutes in FIG. 15, and FIG. 17 shows a zoom scan spectrum of the same peak as in FIG. 16.

Figure 18:
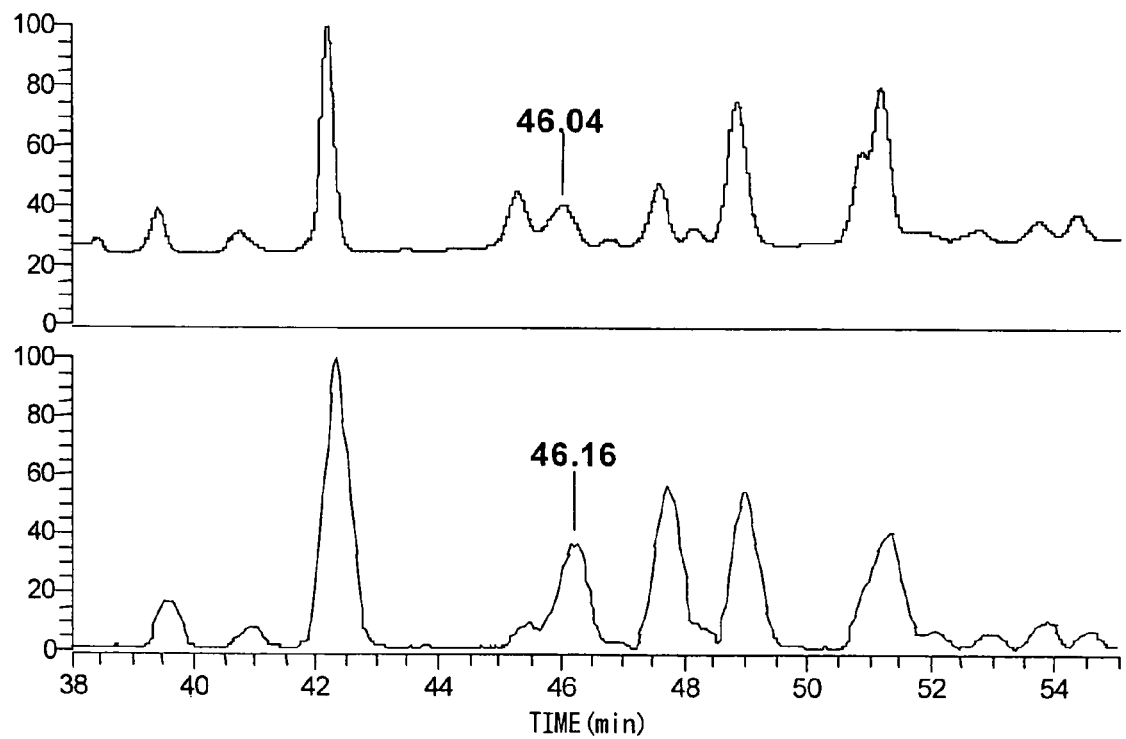
FIG. 18 shows the result (on the peak in FIG. 17C) of liquid chromatography in the LC-MS/MS analysis of a peptide obtained by the reduction/carboxymethylation of the humanized PM-1 antibody subtype 1 followed by trypsin digestion, in which the top is a chromatogram detected by a UV at 215 nm and the bottom is a base peak chromatogram.
Figure 19:
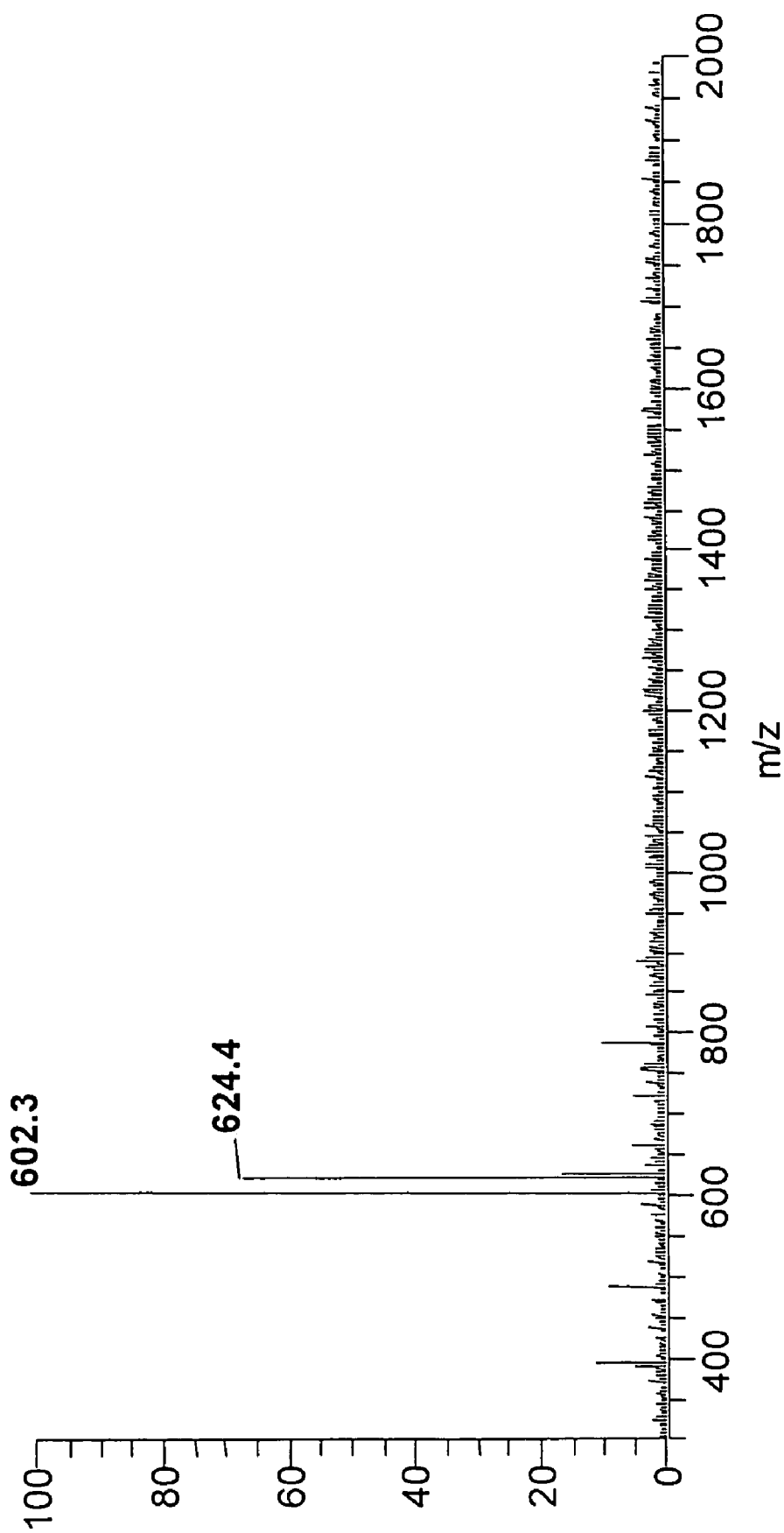
FIG. 19 shows a mass spectrum of the peak at a retention time of 46 minutes in FIG. 18.
Figure 20:
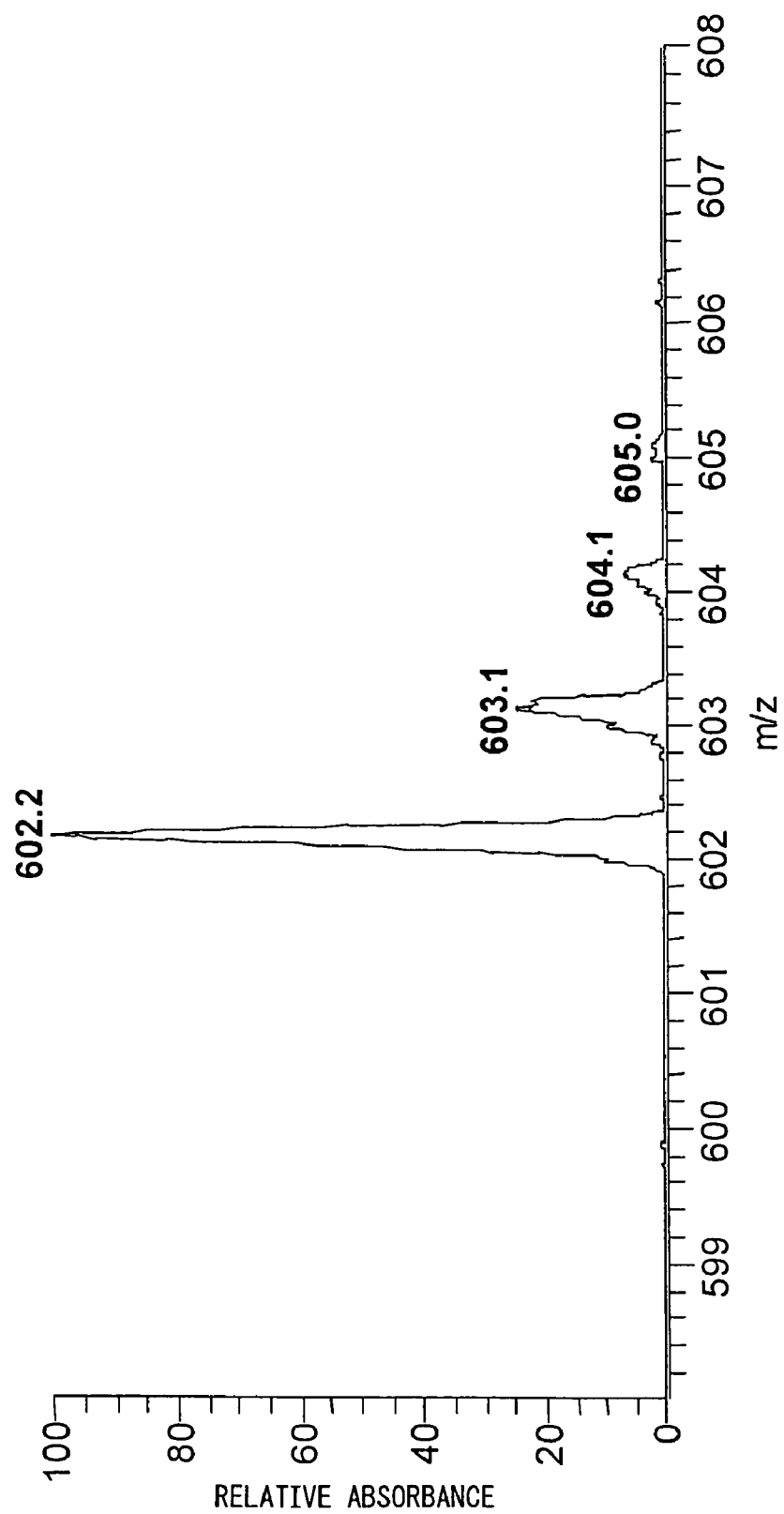
FIG. 20 shows a zoom scan spectrum of the same peak as in FIG. 19.

FIG. 18 to FIG. 20 show the result (on the peak in FIG. 14C) of LC-MS/MS analysis of a peptide obtained by the reduction/carboxymethylation of the humanized PM-1 antibody subtype 1 followed by trypsin digestion. In FIG. 18, the top is a chromatogram detected by a UV at 215 nm and the bottom is a base peak chromatogram. FIG. 19 shows a mass spectrum of the peak at a retention time of 46 minutes in FIG. 18, and FIG. 20 shows a zoom scan spectrum of the same peak as in FIG. 19.

From these results, the detected peak was shown to have the amino acid sequences SLSLSPG (SEQ ID NO: 5) and SLSLSP-NH$_2$ (SEQ ID NO: 4). Thus, it was demonstrated that one of the H chain C-terminals of the humanized PM-1 antibody subtype 1 has the -SLSLSPG sequence (SEQ ID NO: 5), and the other has the -SLSLSPG-NH$_2$ sequence of SEQ ID NO: 6).

(c) Analysis of the Structure of the H Chain C-Terminal of the Humanized PM-1 Antibody Subtype 2

Figure 21:
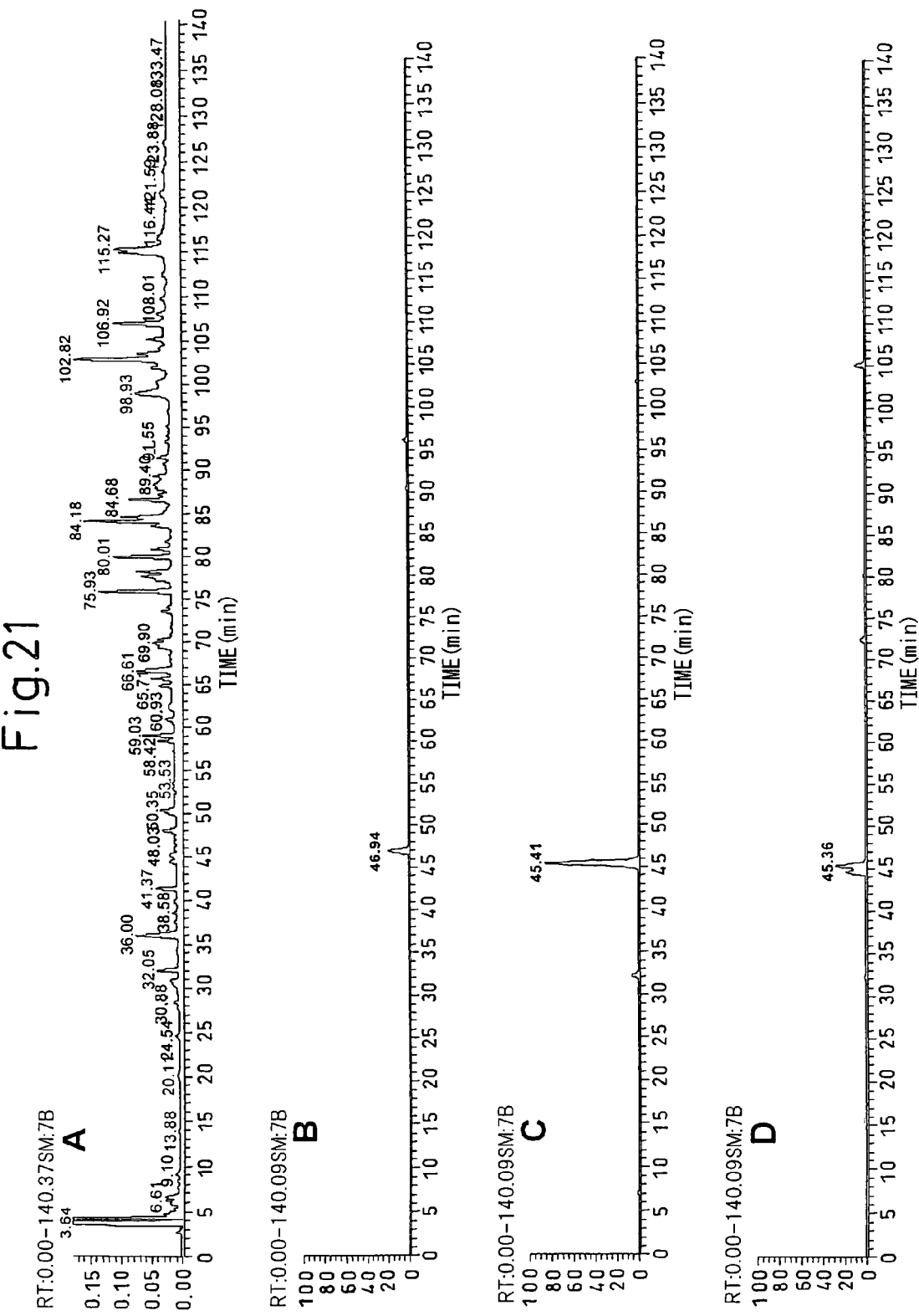
FIG. 21A shows a peptide map of peptides obtained by the reduction/carboxymethylation of the humanized PM-1 antibody subtype 2 followed by trypsin digestion.
FIG. 21B shows the MS chromatogram of molecular weight of SLSLSPG (SEQ ID NO: 5) (selective monitoring at m/z 660.3±0.5)
FIG. 21C shows that of SLSLSP-NH$_2$ (SEQ ID NO: 4) (selective monitoring at m/z 602.3±0.5)
FIG. 21D shows that of SLSLSP (SEQ ID NO: 3) (selective monitoring at m/z 603.3±0.5).

FIG. 21A shows a peptide map of peptides obtained by the reduction/carboxymethylation of the humanized PM-1 antibody subtype 2 followed by trypsin digestion. In order to investigate the structure of the C-terminal fragment of the H chain, FIG. 21B shows the MS chromatogram of molecular weight of SLSLSPG (SEQ ID NO: 5) (selective monitoring at m/z 660.3±0.5), FIG. 21C shows that of SLSLSP-NH$_2$ (SEQ ID NO: 4) (selective monitoring at m/z 602.3±0.5), and FIG. 21 D shows that of SLSLSP (SEQ ID NO: 3) (selective monitoring at m/z 603.3±0.5). Though a peak corresponding to SLSLSPG (SEQ ID NO: 5) was slightly detected, a peak corresponding to SLSLSP-NH$_2$ (SEQ ID NO: 4) was more strongly noted (though a peak with a molecular weight of 603.3 was noted at about 45 minutes in FIG. 21D, it is not SLSLSP (SEQ ID NO: 3), based on the retention time).

Figure 22:
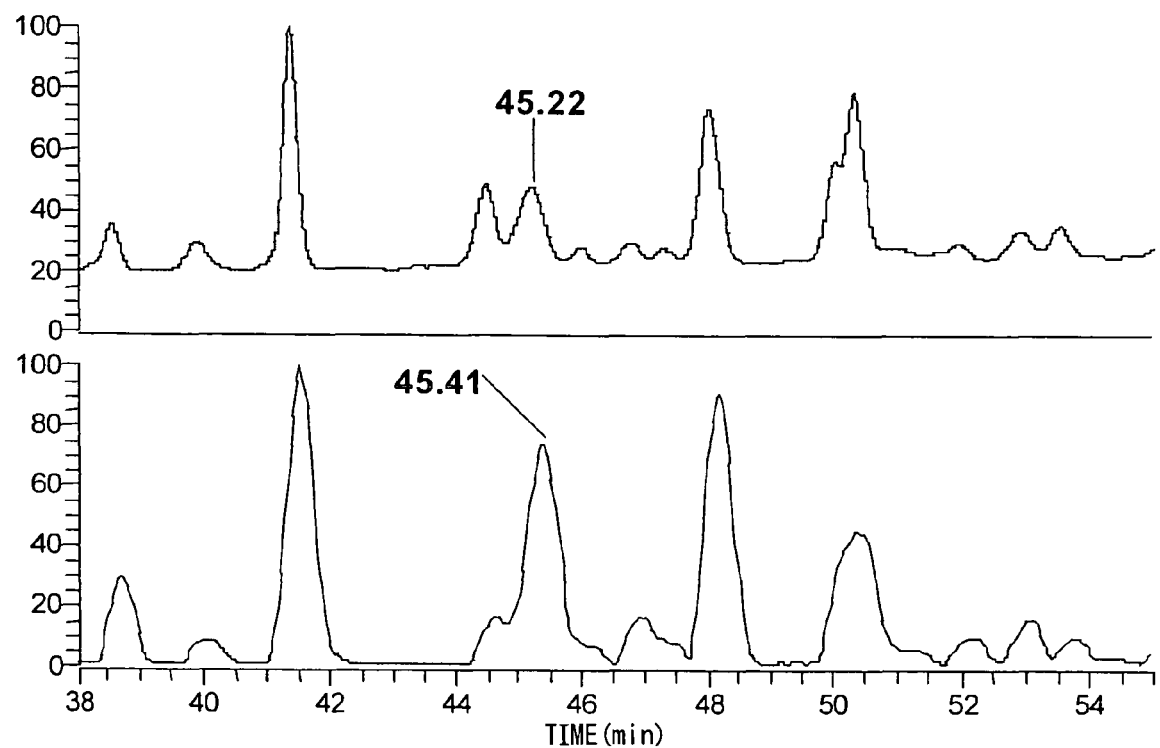
FIG. 22 shows the result of liquid chromatography in the LC-MS/MS analysis of a peptide obtained by the reduction/carboxymethylation of the humanized PM-1 antibody subtype 2 followed by trypsin digestion, in which the top is a chromatogram detected by a UV at 215 nm and the bottom is a base peak chromatogram.
Figure 23:
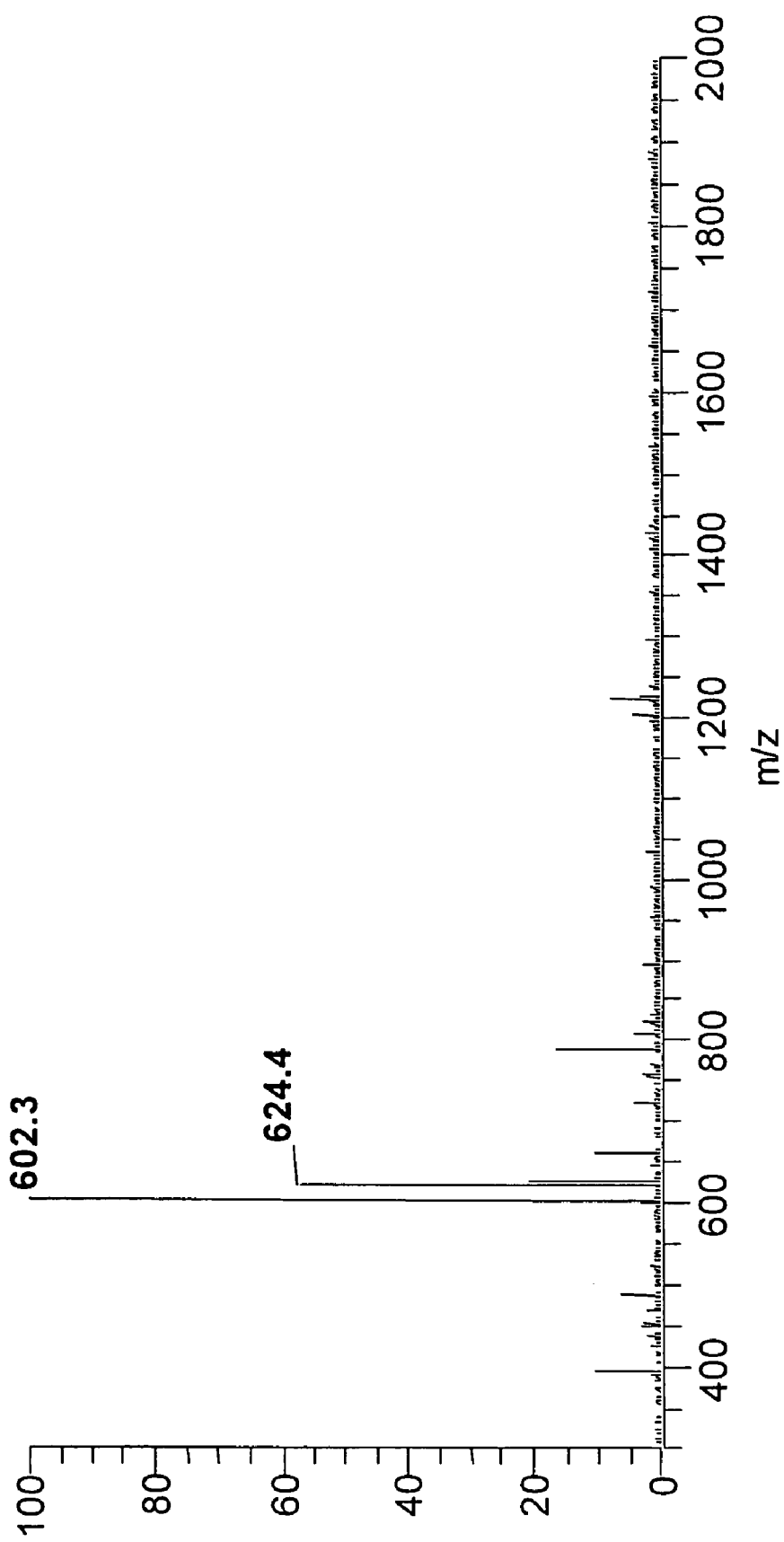
FIG. 23 shows a mass spectrum of the peak at a retention time of 45 minutes in FIG. 22.
Figure 24:
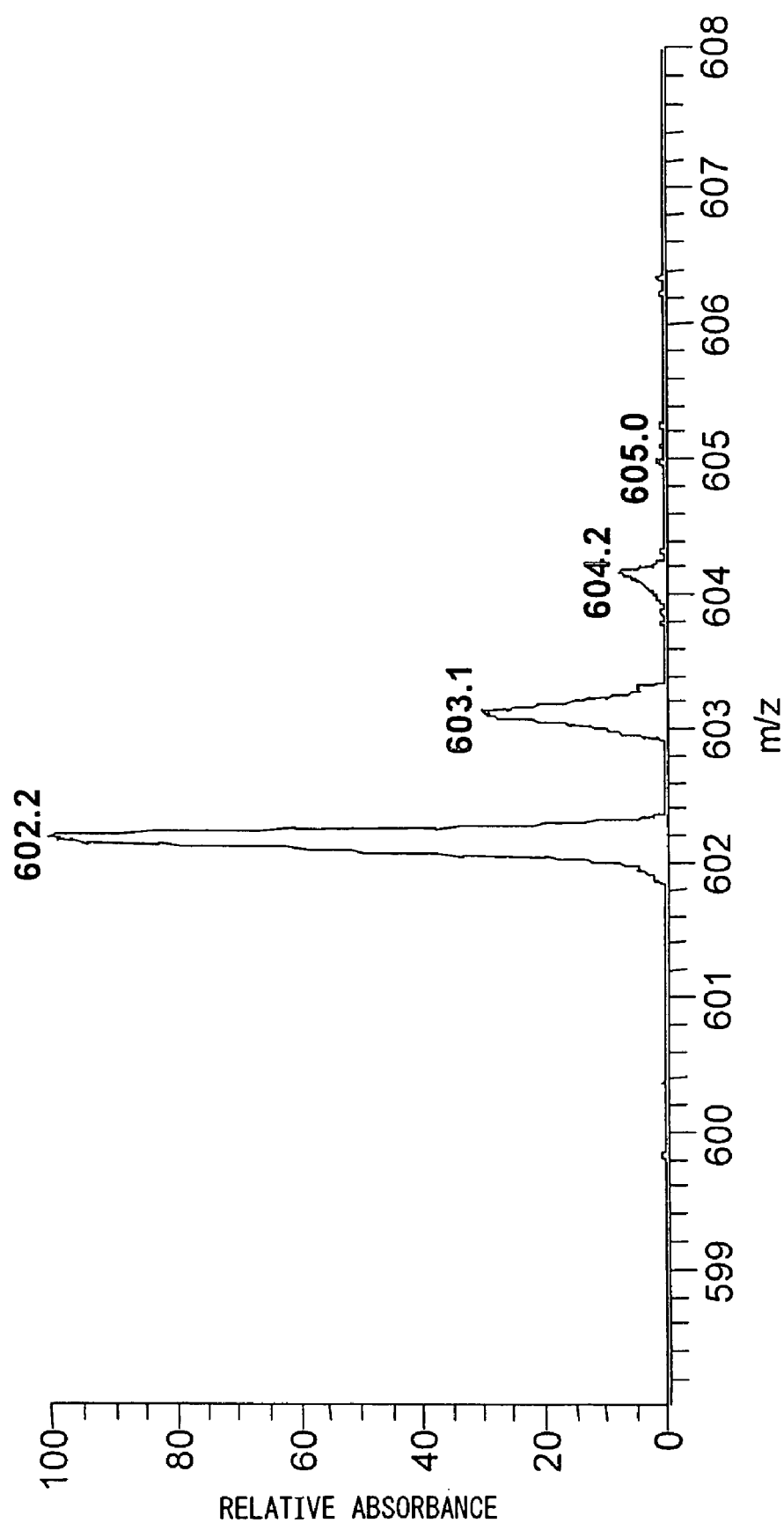
FIG. 24 shows a zoom scan spectrum of the same peak as in FIG. 23.

FIG. 22 to FIG. 24 show the result of LC-MS/MS analysis of a peptide obtained by the reduction/carboxymethylation of the humanized PM-1 antibody subtype 2 followed by trypsin digestion. In FIG. 22, the top is a chromatogram detected by a UV at 215 nm and the bottom is a base peak chromatogram. FIG. 23 shows a mass spectrum of the peak at a retention time of 45 minutes in FIG. 22, and FIG. 24 shows a zoom scan spectrum of the same peak as in FIG. 23. From these results, the detected peak was shown to have the amino acid sequence SLSLSP-NH$_2$ (SEQ ID NO: 4). Thus, it was demonstrated that both of the H chain C-terminals of the humanized PM-1 antibody subtype 2 have the -SLSLSPG-NH$_2$ sequence (SEQ ID NO: 6).

Example 3

Measurement of Biological Activity of the Humanized PM-1 Antibody Subtype 1 and Subtype 2

(1) Determination of IL-6 Receptor-Binding Activity
(a) Method of Determination

The method of determination is as described in the following steps.

1) One hundred µl of anti-IL-6 receptor antibody diluted to 5 µg/ml with a sodium carbonate buffer, pH 9.6, is added to each well of an immunoplate, and allowed to stand in a cold place overnight or longer.

2) Each well is washed three times with 300 µl of a phosphate buffered saline (hereinafter referred to as RB) containing 0.05% polysorbate 20.

3) To each well, 200 μl of a Tris-HCl buffer, pH 8.1 (hereinafter referred to as DB), containing 1% bovine serum albumin is added, and allowed to stand at room temperature for 2 hours or longer.

4) After the liquid in the well is discarded, 100 μl of a soluble IL-6 receptor diluted to 0.1 μg/ml with DB is added to each well, and allowed to stand at room temperature for 2 hours.

5) Each well is washed three times with 300 μl of RB.

6) To each well, 100 μl of a sample solution serially diluted with a DB containing a given amount of biotinylated MRA is added, and allowed to stand at room temperature for 1 hour.

7) Each well is washed three times with 300 μl of RB.

8) To each well, 100 μl of a alkaline phosphatase-labelled streptoavidin diluted to 0.5 μg/ml with DB is added, and allowed to stand at room temperature for 1 hour.

9) Each well of the immunoplate is washed five times with 300 μl of RB.

10) A chromogenic reagent (SIGMA FAST p-nitrophenyl phosphate) is dissolved with water, and 100 μl of it is added to each well, and allowed to stand at room temperature for 30 minutes.

11) The difference in absorbance at 405 nm and that at 655 nm of the reaction in each well is determined.

12) From the absorbance obtained, the binding activity of each sample is calculated using a parallel line test (3+3).

(b) Result

The result is shown in Table 1.

TABLE 1

Antigen-binding activity of humanized PM-1 antibody subtypes

| Subtype | Activity | Specific activity |
|---|---|---|
| Native (Main) | $1.04 \times 10^3$ | 100% |
| Subtype 1 | $1.13 \times 10^3$ | 109% |
| Subtype 2 | $1.12 \times 10^3$ | 108% |

The result in Table 1 reveals that the humanized PM-1 antibody (Main), Subtype 1, and Subtype 2 have substantially the same antigen-binding activity.

(2) Inhibition of KT-3 Cell Growth (a) Method of Determination

The method of determination is as described in the following steps.

1) To each well of a microplate, 50 μl of an IL-6 solution diluted to 2 ng/ml with a RPMI medium is added, and then 50 μl of a sample solution serially diluted with a RPMI medium is added. To a blank well, 50 μl of the RPMI medium is added.

2) Furthermore, 100 μl of a KT-3 cell suspension adjusted to $5 \times 10^4$ cells/ml with the RPMI medium is added to each well, and cultured in a $CO_2$ incubator for 3 days.

3) To each well, 50 μl of a $^3$H-thymidine solution appropriately diluted with the RPMI medium is added, and cultured in the $CO_2$ incubator for 6 days.

4) The cells in the microplate are collected on a glass filter using a cell harvester.

5) After drying the glass filter in a microwave oven for 10 minutes, a solid scintillator is impregnated into the glass filter under heating with a hot plate etc.

6) Using a liquid scintillation counter, radioactivity (cpm) is measured.

7) From the radioactivity obtained, the biological activity of each sample is calculated by a parallel line test (4+4).

The result is shown in Table 2.

TABLE 2

Activity of inhibiting cell growth of humanized PM-1 antibody subtypes

| Subtype | Activity | Specific activity |
|---|---|---|
| Native (Main) | $1.00 \times 10^3$ | 100% |
| Subtype 1 | $1.02 \times 10^3$ | 102% |
| Subtype 2 | $1.01 \times 10^3$ | 101% |

The result in Table 2 reveals that the humanized PM-1 antibody (Main), Subtype 1, and Subtype 2 have substantially the same activity of inhibiting cell growth.

The invention claimed is:

1. An antibody subtype (1) which is a subtype of the humanized PM-1 antibody against interleukin-6 receptor (IL-6R) comprising a heavy chain that has amino acids 1-448 of the amino acid sequence set forth in SEQ ID NO: 1, a heavy chain that has amino acids 1-447 of the amino acid sequence set forth in SEQ ID NO: 1 and a C-terminal that is Pro-NH$_2$, and a light chain that has the amino acid sequence set forth in SEQ ID NO: 2.

2. The antibody subtype according to claim 1 wherein glutamine (Gln) at the heavy chain N-terminal is replaced with pyroglutamic acid (pGlu).

3. A pharmaceutical composition comprising the antibody subtype according to claim 2.

4. A pharmaceutical composition comprising the antibody subtype (1) of claim 1.

5. An antibody subtype (2) which is a subtype of the humanized PM-1 antibody against interleukin-6 receptor (IL-6R) in which both heavy chains have amino acids 1-447 of the amino acid sequence set forth in SEQ ID NO: 1 and a C-terminal that is Pro-NH$_2$, and comprising a light chain that has the amino acid sequence set forth in SEQ ID NO: 2.

6. A pharmaceutical composition comprising the antibody subtype (2) of claim 4.

7. The antibody subtype according to claim 4 wherein glutamine (Gln) at the heavy chain N-terminal is replaced with pyroglutamic acid (pGlu).

8. A pharmaceutical composition comprising the antibody subtype according to claim 7.

9. A pharmaceutical composition comprising the antibody subtype according to claim 2 and the antibody subtype according to claim 7.

10. A pharmaceutical composition comprising:
an antibody subtype (1) which is a subtype of the humanized PM-1 antibody against interleukin-6 receptor (IL-6R) comprising a heavy chain that has amino acids 1-448 of the amino acid sequence set forth in SEQ ID NO: 1, a heavy chain that has amino acids 1-447 of the amino acid sequence set forth in SEQ ID NO: 1 and a C-terminal that is Pro-NH$_2$, and a light chain that has the amino acid sequence set forth in SEQ ID NO: 2; and
an antibody subtype (2) which is a subtype of the humanized PM-1 antibody against interleukin-6 receptor (IL-6R) in which both heavy chains have amino acids 1-447 of an amino acid sequence set forth in SEQ ID NO: 1 and a C-terminal that is Pro-NH$_2$, and comprising a light chain that has the amino acid sequence set forth in SEQ ID NO: 2.

* * * * *

UNITED STATES PATENT AND TRADEMARK OFFICE
CERTIFICATE OF CORRECTION

PATENT NO. : 8,398,980 B2  
APPLICATION NO. : 10/593786  
DATED : March 19, 2013  
INVENTOR(S) : Katsuhiro Kano et al.

Page 1 of 1

It is certified that error appears in the above-identified patent and that said Letters Patent is hereby corrected as shown below:

Title Page, Item 54 and in the specification, Column 1, line 1, Title:

Please replace "INTERLEUKEN-6" with --INTERLEUKIN-6--.

In the claims:

In Claim 6:

Column 21, line 44; please replace "claim 4" with --claim 5--.

In Claim 7:

Column 22, line 21; please replace "claim 4" with --claim 5--.

In Claim 10:

Column 22, line 39; please replace "of an amino acid" with --of the amino acid--.

Signed and Sealed this  
Eighteenth Day of June, 2013

Teresa Stanek Rea  
*Acting Director of the United States Patent and Trademark Office*

UNITED STATES PATENT AND TRADEMARK OFFICE
CERTIFICATE OF CORRECTION

| | |
|---|---|
| PATENT NO. | : 8,398,980 B2 |
| APPLICATION NO. | : 10/593786 |
| DATED | : March 19, 2013 |
| INVENTOR(S) | : Kano et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1068 days.

Signed and Sealed this
Sixth Day of December, 2022

Katherine Kelly Vidal
*Director of the United States Patent and Trademark Office*

SEQUENCE LISTING

<160> NUMBER OF SEQ ID NOS: 6

<210> SEQ ID NO 1
<211> LENGTH: 448
<212> TYPE: PRT
<213> ORGANISM: Artificial Sequence
<220> FEATURE:
<223> OTHER INFORMATION: Amino acid sequence of H chain of humanized
      antibody PM-1 against interleukin-6 receptor

<400> SEQUENCE: 1

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

```
Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 2
<211> LENGTH: 214
<212> TYPE: PRT
<213> ORGANISM: Artificial Sequence
<220> FEATURE:
<223> OTHER INFORMATION: Amino acid sequence of L chain of humanized
      antibody PM-1 against interleukin-6 receptor

<400> SEQUENCE: 2
```

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Ser Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu His Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Asn Thr Leu Pro Tyr
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 6
<212> TYPE: PRT
<213> ORGANISM: Artificial Sequence
<220> FEATURE:
<223> OTHER INFORMATION: Synthesized Construct

<400> SEQUENCE: 3

Ser Leu Ser Leu Ser Pro
 1               5

<210> SEQ ID NO 4
<211> LENGTH: 6
<212> TYPE: PRT
<213> ORGANISM: Artificial Sequence
<220> FEATURE:
<223> OTHER INFORMATION: Synthesized Construct
<221> NAME/KEY: VARIANT
<222> LOCATION: (1)...(6)
<223> OTHER INFORMATION: Xaa = Amidated Proline

<400> SEQUENCE: 4

Ser Leu Ser Leu Ser Xaa
 1               5

<210> SEQ ID NO 5
<211> LENGTH: 7
<212> TYPE: PRT
<213> ORGANISM: Artificial Sequence
<220> FEATURE:
<223> OTHER INFORMATION: Synthesized Construct

<400> SEQUENCE: 5
```

```
Ser Leu Ser Leu Ser Pro Gly
 1               5

<210> SEQ ID NO 6
<211> LENGTH: 7
<212> TYPE: PRT
<213> ORGANISM: Artificial Sequence
<220> FEATURE:
<223> OTHER INFORMATION: Synthesized Construct
<221> NAME/KEY: VARIANT
<222> LOCATION: (1)...(7)
<223> OTHER INFORMATION: Xaa = Amidated Glycine

<400> SEQUENCE: 6

Ser Leu Ser Leu Ser Pro Xaa
 1               5
```